US008710264B2

(12) United States Patent
Rodríguez Vicente et al.

(10) Patent No.: US 8,710,264 B2
(45) Date of Patent: Apr. 29, 2014

(54) ANTITUMORAL COMPOUNDS

(75) Inventors: Alberto Rodríguez Vicente, Madrid (ES); Maria Garranzo García-Ibarrola, Madrid (ES); Carmen Murcia Pérez, Madrid (ES); Francisco Sánchez Sancho, Madrid (ES); Maria del Carmen Cuevas Marchante, Madrid (ES); Cristina Mateo Urbano, Madrid (ES); Isabel Digón Juárez, Madrid (ES)

(73) Assignee: Pharma Mar, S.A., Madrid (ES)

( * ) Notice: Subject to any disclaimer, the term of this patent is extended or adjusted under 35 U.S.C. 154(b) by 481 days.

(21) Appl. No.: 12/746,966

(22) PCT Filed: Dec. 19, 2008

(86) PCT No.: PCT/EP2008/068065
§ 371 (c)(1),
(2), (4) Date: Jun. 9, 2010

(87) PCT Pub. No.: WO2009/080769
PCT Pub. Date: Jul. 2, 2009

(65) Prior Publication Data
US 2010/0280108 A1 Nov. 4, 2010
US 2012/0041063 A2 Feb. 16, 2012

(30) Foreign Application Priority Data

Dec. 20, 2007 (EP) .................................... 07123882

(51) Int. Cl.
*C07C 239/00* (2006.01)
(52) U.S. Cl.
USPC ........................................................ 564/158
(58) Field of Classification Search
None
See application file for complete search history.

(56) References Cited

U.S. PATENT DOCUMENTS

| 4,855,086 | A | * | 8/1989 | Black et al. ................ 514/617 |
| 7,446,196 | B2 | | 11/2008 | Dong et al. |
| 7,655,808 | B2 | | 2/2010 | Dong et al. |

FOREIGN PATENT DOCUMENTS

| CL | 01390-1993 | 5/1994 |
| CL | 02347-1997 | 5/1998 |
| CL | 02072-1999 | 3/2000 |
| CL | 02073-1999 | 3/2000 |
| EP | 0 111 105 A2 | 6/1984 |
| WO | 2005/014574 A1 | 2/2005 |
| WO | WO 2005/117894 | 12/2005 |
| WO | 2007/144423 A1 | 12/2007 |

OTHER PUBLICATIONS

Silverman (The Organic Chemistry of Drug Design and Drug Action, 1992, Academic Press Inc.).*

U.S. Appl. No. 12/304,123, filed Jan. 26, 2009, Ma Jesus Martin Lopez.
U.S. Appl. No. 12/746,974, filed Jun. 9, 2010, Alberto Rodriguez Vicente.
Boyd, M. et al. "Some Practical Considerations and Applications of the National Cancer institute in Vitro Anticancer Drug Discovery Screen" *Drug Dev, Res.* 1995, 34, 91-109.
Dorwald, "Side Reactions in Organic Synthesis," Wiley-VCH, Weinheim, p. IX of preface, pp. 1-15, 2005.
Faircloth, G. T. et al. "A simple screening procedure for the quantitative measurement of cytotoxicity to resting primary lymphocyte cultures" *J. Tiss. Cult. Meth.* 1988, 11, 201-205.
Gudasheva O. A. et al. "Synthesis, conformation análisis, and anxiolytic activity of retropeptide analogs of 4-cholecystokinin" *Pharm. Chem. J.* 2006, 40, 367-372.
Gudasheva, T. A. et al. "Design and Synthesis of Cholecystokinin-4 Dipeptide Analogues with Anxiolytic and Anxiogenic Activities" *Russ. J. Bioorg. Chem.* 2007, 33, 383-389.
Gunasekera, S. P. et al. "Discodermolide: A new Bioactive Polyhydroxylated Lactone from the Marine Sponge Discodermia dissolute" *J. Org. Chem.* 1990, 55, 4912-4915; *J. Org. Chem.* 1991, 56, 1346.
Haar, E. et al. "Discodermolide, A Cytotoxic Marine Agent that Stabilizes Microtubules more Potently than Taxol" 1996, 35, 243-250.
Hung, D. T. et al. "(+)-Discodermolide binds to microtubuies in stechiometric ratio to tubulin dimmers, blocks taxol binding and results in mitotic arrest" *Chem. Biol.* 1996; 3, 287-293.
Jansen, R. et al. "Antibiotics from Gliding Bacteria, LXXXIII. The Crocains, Novel Antifungal and Cytotoxic Antibiotics from *Chrondomyces crocatus* and *Chondromyces pediculatus* (Myxobacteria): Isolation and Structure Elucidation" 1999, 1085-1089.
Kuhnt, M et al. "Microbial Conversion Products of Leptomycin B" Applied and Environmental Microbiology, Feb. 1998, 714-720.
Kunze, B. et al. "Crocacin, a New Electron Transport inhibitor from *Chondromyces crocatus* (Myxobacteria). Production, Isolation, Physico-chemical and biological properties" *J. Antibiot.* 1994, 47, 881-886.
Mosmann, T. et al. "Rapid Colorimetric Assay for Cellular Growth and Survival: Application to Proliferation and Citotoxicity Assays" *J. Inmunol. Meth.* 1983, 65, 55-63.
Phukan, P. et al. "Flexible Routes to the 5-Hydroxy Acid Fragment of the Cryptophycins" 2003, 1733-1740.
Pla, D. et al. "Modular Total Synthesis of Lamellarin D" *J. Org, Chem.* 2005, 70, 8231-8234.

(Continued)

*Primary Examiner* — Johann R Richter
*Assistant Examiner* — Jennifer C Sawyer
(74) *Attorney, Agent, or Firm* — Lando & Anastasi LLP

(57) ABSTRACT

A compound of general formula (I)

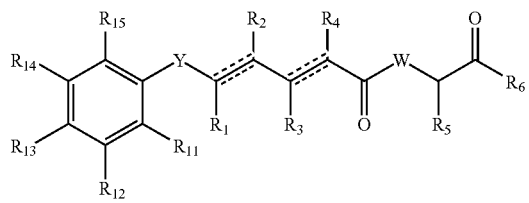

wherein, $R_{11}$, $R_{12}$, $R_{13}$, $R_{14}$, $R_{15}$, W, Y, $R_1$, $R_2$, $R_3$, $R_4$, $R_5$, and $R_6$ take various meanings for use in the treatment of cancer.

20 Claims, No Drawings

(56) References Cited

OTHER PUBLICATIONS

Pozdnev, V. F. et al. "Activation of carboxilic acids by pyrocarbonates. Application of Di-tert-butyl pyrocarbonate as condensing reagent in the synthesis of amides of protected amino acids and peptides" *Tetrahedron Lett.* 1995, 36, 7115-7118.

Schiff P. B. et al. "Promotion of microtubule assembly in vitro by taxol" *Nature* 1979, 227, 665-667.

Skehan, P. et al. "New Colorimetric Cytotoxicity Assay for Anticancer-Drug Screening" *J. Natl. Cancer Inst.*, 1990, 82, 1107-1112.

Stork, G. et al. "A stereoselctive synthesis of (Z)-1-iodo-1-alkenes" *Tetrahedron Lett.* 1989, 30, 2173-2174.

Takeuchi, R. et al. "Stereodivergent Synthesis of (E)- and (Z)-2-Alken-4-yn-1-ols from 2-Propynoic Acid: A Practical Route via 2-Alken-4-ynoates" *J. Org. Chem.* 2000, 55, 1556-1561.

Wolff, "Burger's Medicinal Chemistry and Drug Discovery," vol. 1, Principles and Practice, John Wiley & Sons, New York, pp. 975-977, 1997.

Banker, Gilbert S. et al., Modern Pharmaceutics, Marcel Dekker, New York, pp. 451 & 596, 1996.

Greyer et al., "The National Cancer Institute: Cancer Drug Discovery and Development Program," Seminars in Oncology, vol. 19, No. 6, pp. 622-638, Dec. 1992.

Gulledge et al: "Microcystin Analogues Comprised Only of Adda and a Single Additional Amino Acid Retain Moderate Activity As PP1/PP2a Inhibitors" Bioorganic & Medicinal Chemistry Letters, Pergamon, Elsevier Science, GB, vol. 13, No. 17, Sep. 1, 2003, pp. 2907-2911.

Hermann et al: "Total Synthesis of 1-27 Hapalosin and Two Ring Expanded Analogs" Tetrahedron, Elsevier Science Publishers, Amsterdam, NL, vol. 56, No. 43, Oct. 20, 2000, pp. 8461-8471.

International Preliminary Report on Patentability & Written Opinion for PCT/EP07/055959, dated Dec. 16, 2008.

International Preliminary Report on Patentability & Written Opinion for PCT/EP08/68049, dated Jun. 22, 2010.

International Preliminary Report on Patentability & Written Opinion for PCT/EP08/68065, dated Jun. 22, 2010.

International Search Report for PCT/EP07/055959, dated Feb. 10, 2007.

International Search Report for PCT/EP08/68065, dated Jul. 2, 2009.

International Search Report nofor PCT/EP08/68049, dated Jun. 22, 2010.

Jayasuriya, "Alkyl Electrophiles in Pd-Catalyzed Cross-Coupling Reactions", Frontiers of Chemistry, 2005, 1-21.

Jones et al: "Microbial modification of mycophenolic acid" Journal of the Chemical Society, Section C: Organic Chemistry, Chemical Society. Letchworth, GB, val. 12, Jan. 1, 1970, pp. 1725-1737, XP002165092 ISSN: 0022-4952.

Kalesse et al. "The Chemistry and Biology of the Leptomycin Family", Synthesis, 2002, p. 981-1003.

Lipomi et al., "Total Synthesis of Basiliskamides A and B," Organic Letters, 6(20), pp. 3533-3536, 2004.

Rouchi, "Moving Beyond Natural Products", Chemical and Engineering News, 81(41), 104-107, 2003.

Nicolaou et al., "Total Synthesis of Rapamycin," J. Am. Chem. Soc., 115, pp. 4419-4420, 1993.

Nicolaou et al., "Total Synthesis of the Novel Immunosuppressant Sanglifehrin A," J. Am. Chem. Soc., 122, pp. 3830-3838, 2000.

Paquette et al., "A Convergent Three-Component Total Synthesis of the Powerful Immunosuppressant (+)-Sanglifehrin A," J. Am. Chem. Soc., 124, pp. 4257-4270, 2002.

Parker et al., "The Total Synthesis of (−)-SNF4435 C and (+)-SNF 4435 D," J. Am. Chem. Soc., 126, pp. 15968-15969, 2004.

Paterson et al., "Total Synthesis and Configurational Assignment of (−)-Dictyostatin, a Microtubule-Stabilizing Macrolide of Marine Sponge Origin," Angewandte Chemie Int. Ed., 43, pp. 4629-4633, 2004.

Schmid et al., "Total Synthesis of Monensin, 1, Stereocontrolled Synthesis of the Lef Half of Monensin," Journal of the American Chemical Society, p. 259-260, 1979.

Smith et al., "(+)-Phorboxazole A Synthetic Studies. A Highly Convergent, Second Generation Total Synthesis of (+)-Phorboxazole A," Organic Letters, 7(20), pp. 4399-4402, 2005.

Smith et al., "Total Synthesis of Rapamycin and Demethoxyrapamycin," J. Am. Chem. Soc., 117, pp. 5407-5408, 1995.

Suggitt et al., "50 Years of Preclinical Anticancer Drug Screening: Empirical to Target-Driven Approaches," Clinical Cancer Research, vol. 11, Feb. 1, 2005, pp. 971-981.

Williams et al., "Total Synthesis of (+)-Amphidinolide J," J. Am. Chem. Soc., 120, pp. 11198-11199, 1998.

\* cited by examiner

ANTITUMORAL COMPOUNDS

FIELD OF THE INVENTION

The present invention relates to new antitumoral compounds, pharmaceutical compositions containing them and their use as antitumoral agents.

BACKGROUND OF THE INVENTION

In 1990, Gunasekera S P et al. reported the isolation of a new polyhydroxylated lactone, (+)-discodermolide, from the deep-water Caribbean sponge *Discodermia dissoluta* (Gunasekera S P et al. J. Org. Chem. 1990, 55, 4912-4915 and J. Org. Chem. 1991, 56, 1346).

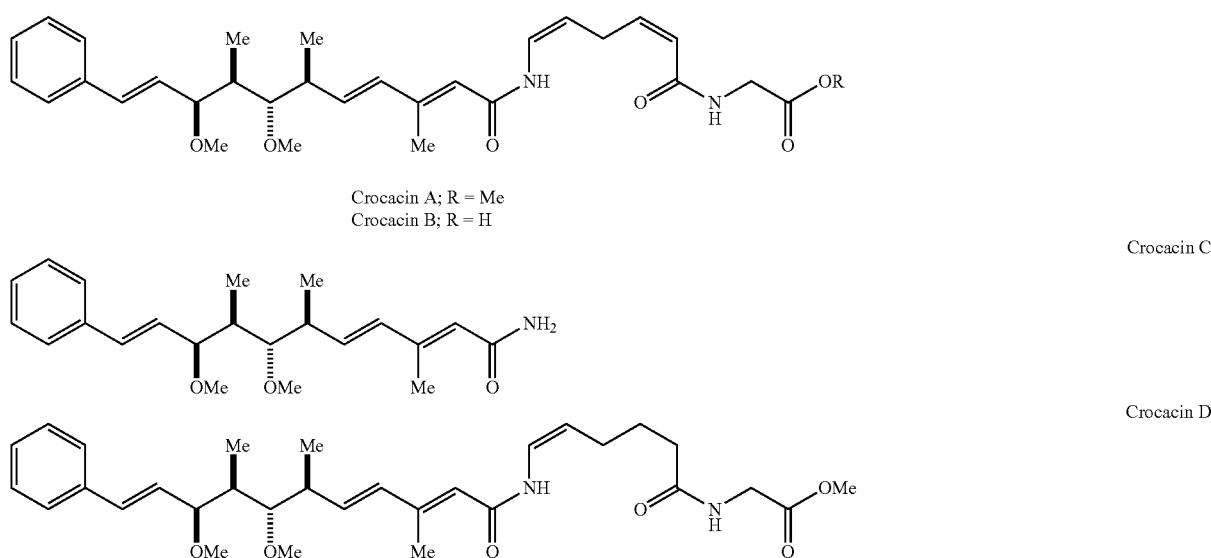

This compound has been revealed to be a potent antimitotic agent (Hung D T et al. Chem. Biol. 1996, 3, 287-293 and ter Haar E et al. Biochemistry 1996, 35, 243-250), possessing a mode of action similar to that of the clinically proven anticancer agent paclitaxel (Schiff P B et al. Nature 1979, 277, 665-667). Both natural products arrest the cell cycle at the M phase, promote microtubule formation, and have similar inhibitory effects against breast cancer carcinoma ($IC_{50}$ of 2.4 nM and 2.1 nM, respectively).

On the other hand, some unusual linear dipeptides containing a N-acyl enamide functionality have been isolated from a myxobacteria belonging to the *Chondromyces* genus (Kunze B et al. J. Antibiot. 1994, 47, 881-886 and Jansen R et al. J. Org. Chem. 1999, 1085-1089). Specifically, these compounds are crocacins A, B, C and D and are a group of electron transport inhibitors.

Crocacins A-D moderately inhibit the growth of a few Gram-positive bacteria and are potent inhibitors of animal cell cultures and several yeasts and fungi. The most active is crocacin D which showed a MIC of 1.4 ng/mL against the fungus *Saccharomyces cerevisiae* and strong toxicity ($IC_{50}$ of 0.06 mg/L) toward L929 mouse fibroblast cell culture.

Gudasheva et al. (Russian Journal of Bioorganic Chemistry, 2007, 44(4), 413-420, and Pharmaceutical Chemistry Journal, 2006, 40(7), 367-372) reported the design of dipeptide compounds based on the structure of the endogenous tetrapeptide cholescystokinin-4 (CCK-4). In this regard, it is disclosed that L-thryptophan derivatives exhibited anxiolytic properties and the D-thryptophan derivatives, anxiogenic properties. Two of the dipeptide compounds disclosed by Gudasheva et al. are the following:

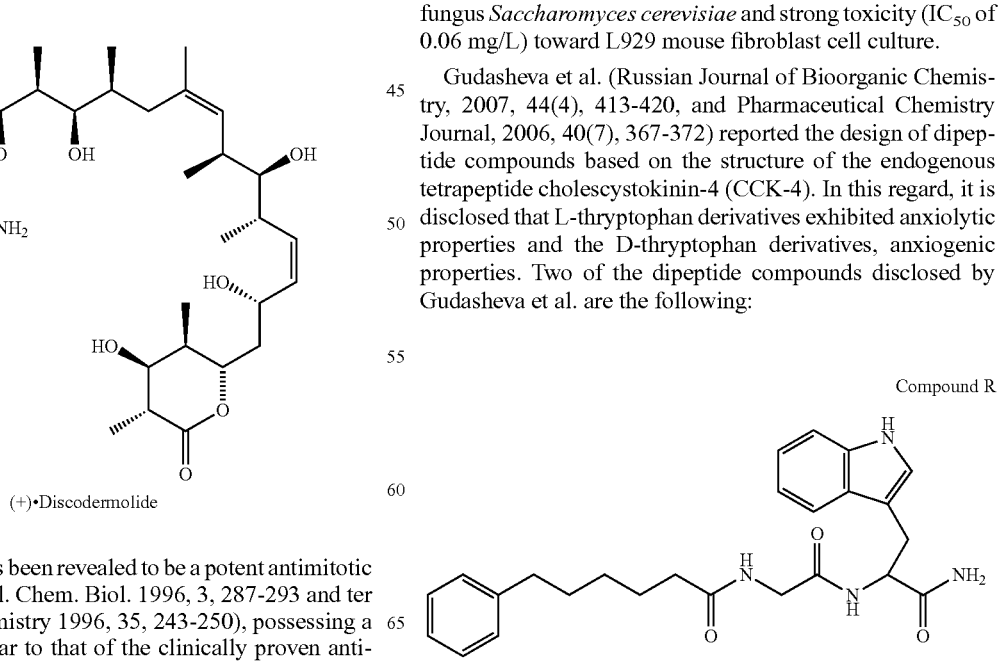

-continued

Compound U

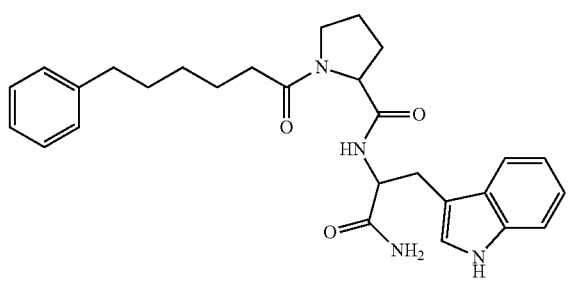

and the following compounds were disclosed as intermediates in the synthesis of compounds R and U:

Compound S

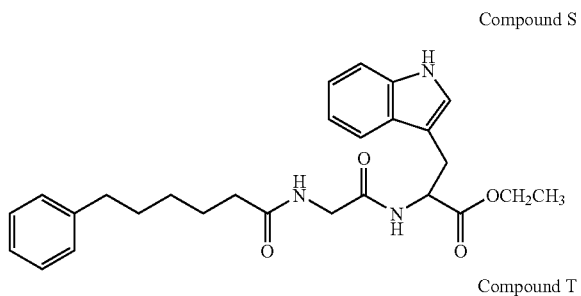

Compound T

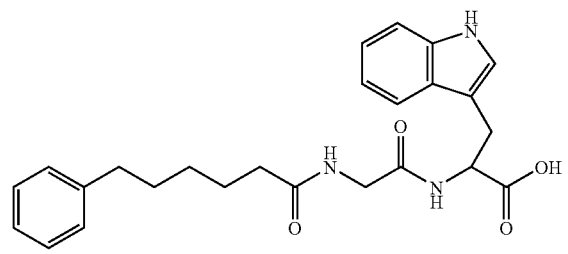

Compound V

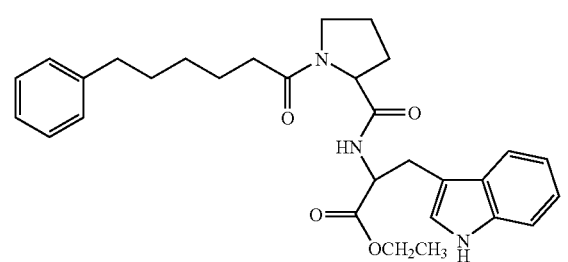

Compound W

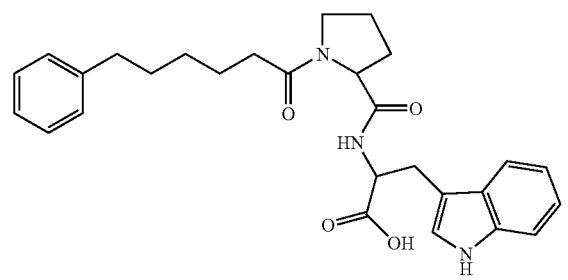

-continued

Compound Y

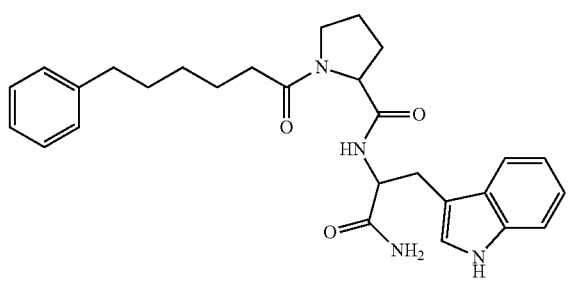

Compound Z

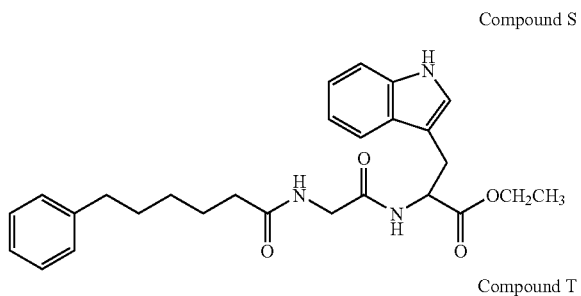

Cancer is a leading cause of death in animals and humans. Huge efforts have been and are still being undertaken in order to obtain an antitumor agent active and safe to be administered to patients suffering from a cancer. The problem to be solved by the present invention is to provide compounds that are useful in the treatment of cancer.

SUMMARY OF THE INVENTION

In one aspect, the present invention is directed to compounds of general formula I or pharmaceutically acceptable salts, tautomers, prodrugs or stereoisomers thereof

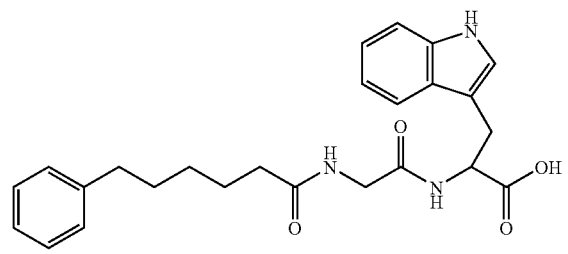

wherein Y is selected from —$CHR_{ay}$—, —$CHR_{ay}$—$CHR_{by}$—, —$CR_{ay}$=$CR_{by}$—, —C≡C—, —$CHR_{ay}$—$CHR_{by}$—$CHR_{cy}$—, —$CHR_{ay}$—$CR_{by}$=$CR_{cy}$—, and —$CHR_{ay}$—C≡C—;

each $R_{ay}$, $R_{by}$, and $R_{cy}$ is independently selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

each $R_1$, $R_2$, $R_3$, $R_4$, and $R_5$ is independently selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

$R_6$ is selected from $NR_8R_9$, and $OR_{10}$;

W is selected from O and $NR_7$;

$R_7$ is selected from hydrogen, $COR_a$, $COOR_a$, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl, or $R_7$ and $R_5$ together with the corresponding N atom and C atom to which they are attached may form a substituted or unsubstituted heterocyclic group;

$R_8$ is selected from hydrogen, $COR_a$, $COOR_a$, substituted or unsubstituted $C_2$-$C_{12}$ alkenyl, substituted or unsubstituted $C_2$-$C_{12}$ alkynyl, and substituted or unsubstituted $C_4$-$C_{12}$ alkenynyl;

$R_{10}$ is selected from hydrogen, substituted or unsubstituted $C_2$-$C_{12}$ alkenyl, and substituted or unsubstituted $C_2$-$C_{12}$ alkynyl;

each dotted line represents an optional additional bond with the proviso that one or more additional bonds are present, but when a triple bond exists between the C atoms to which $R_1$ and $R_2$ are attached, $R_1$ and $R_2$ are absent, and when a triple bond exists between the C atoms to which $R_3$ and $R_4$ are attached, $R_3$ and $R_4$ are absent;

$R_9$ is selected from hydrogen, $COR_a$, $COOR_a$, substituted or unsubstituted $C_2$-$C_{12}$ alkenyl, substituted or unsubstituted $C_2$-$C_{12}$ alkynyl, and substituted or unsubstituted $C_4$-$C_{12}$ alkenynyl;

each $R_{11}$, $R_{12}$, $R_{13}$, $R_{14}$, and $R_{15}$ are independently selected from hydrogen, halogen, $OR_a$, $COR_a$, $COOR_a$, $OCOR_a$, $OCOOR_a$; $OCONR_aR_b$, $CONR^aR_b$, $OS(O)R_a$, $OSO_2R_a$, $OP(O)(R_a)OR_b$, $OSiR_aR_bR_c$, $NR_aR_b$, $NR_aCOR_b$, $NR_a$-$CONR_aR_b$, $NR_aS(O)R_b$, $NR_aSO_2R_b$, $NR_aC(=NR_a)NR_aR_b$, $SR_a$, $S(O)R_a$, $SO_2R_a$, $S(O)NR_aR_b$, $SO_2NR_aR_b$, $S(O)OR_a$, $SO_2OR_a$, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl; and each $R_a$, $R_b$, and $R_c$ are independently selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl and substituted or unsubstituted heterocyclic group.

In another aspect, the present invention is also directed to a compound of formula I, or a pharmaceutically acceptable salt, tautomer, prodrug or stereoisomer thereof, for use as medicament In another aspect, the present invention is also directed to a compound of formula I, or a pharmaceutically acceptable salt, tautomer, prodrug or stereoisomer thereof, for use as medicament for treating cancer.

In a further aspect, the present invention is also directed to the use of compounds of formula I, or pharmaceutically acceptable salts, tautomers, prodrugs or stereoisomers thereof, in the treatment of cancer, or in the preparation of a medicament for the treatment of cancer.

Other aspects of the invention are methods of treatment, and compounds for use in these methods. Therefore, the present invention further provides a method of treating any mammal, notably a human, affected by cancer which comprises administering to the affected individual a therapeutically effective amount of a compound of formula I, or a pharmaceutically acceptable salt, tautomer, prodrug or stereoisomer thereof.

In a yet further aspect, the present invention is also directed to a compound of formula I, or a pharmaceutically acceptable salt, tautomer, prodrug or stereoisomer thereof, for use as anticancer agent.

In another aspect, the present invention is directed to pharmaceutical compositions comprising a compound of formula I, or a pharmaceutically acceptable salt, tautomer, prodrug or stereoisomer thereof, together with a pharmaceutically acceptable carrier or diluent.

DETAILED DESCRIPTION OF PREFERRED EMBODIMENTS

The present invention relates to compounds of general formula I as defined above.

In these compounds the groups can be selected in accordance with the following guidance:

Alkyl groups may be branched or unbranched, and preferably have from 1 to about 12 carbon atoms. One more preferred class of alkyl groups has from 1 to about 6 carbon atoms. Even more preferred are alkyl groups having 1, 2, 3 or 4 carbon atoms. Methyl, ethyl, propyl, isopropyl and butyl, including tert-butyl, sec-butyl and isobutyl are particularly preferred alkyl groups in the compounds of the present invention. Another preferred class of alkyl groups has from 6 to about 10 carbon atoms; and even more preferably 7, 8 or 9 carbon atoms. Heptyl, octyl and nonyl are the most preferred alkyl groups of this class.

Preferred alkenyl and alkynyl groups in the compounds of the present invention may be branched or unbranched, have one or more unsaturated linkages and from 2 to about 12 carbon atoms. One more preferred class of alkenyl and alkynyl groups has from 2 to about 6 carbon atoms. Even more preferred are alkenyl and alkynyl groups having 2, 3 or 4 carbon atoms. Another preferred class of alkenyl and alkynyl groups has from 4 to about 10 carbon atoms, still more preferably 6 to about 10 carbon atoms; and even more preferably 7, 8 or 9 carbon atoms.

We define alkenynyl group as an alkyl group containing one or more double bonds and one or more triple bonds, and preferred alkenynyl groups are those having from 4 to about 12 carbon atoms. One more preferred class of alkenynyl groups has from 6 to about 10 carbon atoms.

Suitable aryl groups in the compounds of the present invention include single and multiple ring compounds, including multiple ring compounds that contain separate and/or fused aryl groups. Typical aryl groups contain from 1 to 3 separated or fused rings and from 6 to about 18 carbon ring atoms. Preferably aryl groups contain from 6 to about 10 carbon ring atoms. Specially preferred aryl groups include substituted or unsubstituted phenyl, substituted or unsubstituted naphthyl, substituted or unsubstituted biphenyl, substituted or unsubstituted phenanthryl and substituted or unsubstituted anthryl.

Suitable heterocyclic groups include heteroaromatic and heteroalicyclic groups containing from 1 to 3 separated or fused rings and from 5 to about 18 ring atoms. Preferably heteroaromatic and heteroalicyclic groups contain from 5 to about 10 ring atoms, most preferably 5, 6 or 7 ring atoms. Suitable heteroaromatic groups in the compounds of the present invention contain one, two or three heteroatoms selected from N, O or S atoms and include, e.g., coumarinyl including 8-coumarinyl, quinolyl including 8-quinolyl, isoquinolyl, pyridyl, pyrazinyl, pyrazolyl, pyrimidinyl, furyl, pyrrolyl, thienyl, thiazolyl, isothiazolyl, triazolyl, tetrazolyl, isoxazolyl, oxazolyl, imidazolyl, indolyl, isoindolyl, indazolyl, indolizinyl, phthalazinyl, pteridinyl, purinyl, oxadiazolyl, thiadiazolyl, furazanyl, pyridazinyl, triazinyl, cinnolinyl, benzimidazolyl, benzofuranyl, benzofurazanyl, benzothiophenyl, benzothiazolyl, benzoxazolyl, quinazolinyl, quinoxalinyl, naphthyridinyl and furopyridyl. Suitable heteroalicyclic groups in the compounds of the present invention contain one, two or three heteroatoms selected from N, O or S atoms and include, e.g., pyrrolidinyl, tetrahydrofuranyl, dihydrofuranyl, tetrahydrothienyl, tetrahydrothiopyranyl, piperidyl, morpholinyl, thiomorpholinyl, thioxanyl, piperazinyl, azetidinyl, oxetanyl, thietanyl, homopiperidyl, oxepanyl, thiepanyl, oxazepinyl, diazepinyl, thiazepinyl, 1,2,3,6-tetrahydropyridyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexyl, 3-azabicyclo[4.1.0]heptyl, 3H-indolyl, and quinolizinyl.

The groups above mentioned may be substituted at one or more available positions by one or more suitable groups such as OR', =O, SR', SOR', $SO_2R'$, $NO_2$, NHR', NR'R', =N—R', NHCOR', $N(COR')_2$, $NHSO_2R'$, NR'C(=NR')NR'R', CN, halogen, COR', COOR', OCOR', OCONHR', OCONR'R', CONHR', CONR'R', protected OH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group, wherein each of the R' groups is independently selected from the group consisting of hydrogen, OH, $NO_2$, $NH_2$, SH, CN, halogen, COH, COalkyl, $CO_2H$, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group. Where such groups are themselves substituted, the substituents may be chosen from the foregoing list.

Suitable halogen substituents in the compounds of the present invention include F, Cl, Br and I.

Suitable protecting groups for OH are well known for the skilled person in the art. A general review of protecting groups in organic chemistry is provided by Wuts, P G M and Greene T W in Protecting Groups in Organic Synthesis, $4^{th}$ Ed. Wiley-Interscience, and by Kocienski P J in Protecting Groups, $3^{rd}$ Ed. Georg Thieme Verlag. These references provide sections on protecting groups for OH. All these references are incorporated by reference in their entirety. Examples of such protected OH include ethers, silyl ethers, esters, sulfonates, sulfenates and sulfinates, carbonates and carbamates. In the case of ethers the protecting group for the OH can be selected from methyl, methoxymethyl, methylthiomethyl, (phenyldimethylsilyl)methoxymethyl, benzyloxymethyl, p-methoxybenzyloxymethyl, [(3,4-dimethoxybenzyl)oxy]methyl, p-nitrobenzyloxymethyl, o-nitrobenzyloxymethyl, [(R)-1-(2-nitrophenyl)ethoxy]methyl, (4-methoxyphenoxy)methyl, guaiacolmethyl, [(p-phenylphenyl)oxy]methyl, t-butoxymethyl, 4-pentenyloxymethyl, siloxymethyl, 2-methoxyethoxymethyl, 2-cyanoethoxymethyl, bis(2-chloroethoxy)methyl, 2,2,2-trichloroethoxymethyl, 2-(trimethylsilyl)ethoxymethyl, menthoxymethyl, o-bis(2-acetoxyethoxy)methyl, tetrahydropyranyl, fluorous tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl 5,5-dioxide, 1-[(2-chloro-4-methyl)phenyl]-4-methoxypiperidin-4-yl, 1-(2-fluorophenyl)-4-methoxypiperidin-4-yl, 1-(4-chlorophenyl)-4-methoxypiperidin-4-yl, 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-hydroxyethyl, 2-bromoethyl, 1-[2-(trimethylsilyl)ethoxy]ethyl, 1-methyl-1-methoxyethyl, 1-methyl-1-benzyloxyethyl, 1-methyl-1-benzyloxy-2-fluoroethyl, 1-methyl-1-phenoxyethyl, 2,2,2-trichloroethyl, 1,1-dianisyl-2,2,2-trichloroethyl, 1,1,1,3,3,3-hexafluoro-2-phenylisopropyl, 1-(2-cyanoethoxy)ethyl, 2-trimethylsilylethyl, 2-(benzylthio)ethyl, 2-phenylselenyl)ethyl, t-butyl, cyclohexyl, 1-methyl-1'-cyclopropylmethyl, allyl, prenyl, cinnamyl, propargyl, p-chlorophenyl, p-methoxyphenyl, p-nitrophenyl, 2,4-dinitrophenyl, 2,3,5,6-tetrafluoro-4-(trifluoromethyl)phenyl, benzyl, p-methoxybenzyl, 3,4-dimethoxybenzyl, 2,6-dimethoxybenzyl, o-nitrobenzyl, p-nitrobenzyl, pentadienylnitrobenzyl, pentadienylnitropiperonyl, halobenzyl, 2,6-dichlorobenzyl, 2,4-dichlorobenzyl, 2,6-difluorobenzyl, p-cyanobenzyl, fluorous benzyl, 4-fluorousalkoxybenzyl, trimethylsilylxylyl, p-phenylbenzyl, 2-phenyl-2-propyl, p-acylaminobenzyl, p-azidobenzyl, 4-azido-3-chlorobenzyl, 2-trifluoromethylbenzyl, 4-trifluoromethylbenzyl, p-(methylsulfinyl)benzyl, p-siletanylbenzyl, 4-acetoxybenzyl, 4-(2-trimethylsilyl)ethoxymethoxybenzyl, 2-naphthylmethyl, 2-picolyl, 4-picolyl, 3-methyl-2-picolyl N-oxido, 2-quinolinylmethyl, 6-methoxy-2-(4-methylphenyl-4-quinolinemethyl, 1-pyrenylmethyl, diphenylmethyl, 4-methoxydiphenylmethyl, 4-phenyldiphenylmethyl, p,p'-dinitrobenzhydryl, 5-dibenzosuberyl, triphenylmethyl, tris(4-t-butylphenyl)methyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxy)phenyldiphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 4,4'-dimethoxy-3"-[N-(imidazolylmethyl)]trityl, 4,4'-dimethoxy-3"-[N-(imidazolylethyl)carbamoyl]trityl, bis(4-methoxyphenyl)-1'-pyrenylmethyl, 4-(17-tetrabenzo[a,c,g,i]fluorenylmethyl)-4,4"-dimethoxytrityl, 9-anthryl, 9-(9-phenyl)xanthenyl, 9-phenylthioxanthyl, 9-(9-phenyl-10-oxo)anthryl, 1,3-benzodithiolan-2-yl, and 4,5-bis(ethoxycarbonyl)-[1,3]-dioxolan-2-yl, benzisothiazolyl S,S-dioxido. In the case of silyl ethers the protecting group for the OH can be selected from trimethylsilyl, triethylsilyl, triisopropylsilyl, dimethylisopropylsilyl, diethylisopropylsilyl, dimethylhexylsylil, 2-norbornyldimethylsilyl, t-butyldimethylsilyl, t-butyldiphenylsilyl, tribenzylsilyl, tri-p-xylylsilyl, triphenylsilyl, diphenylmethylsilyl, di-t-butylmethylsilyl, bis(t-butyl)-1-pyrenylmethoxysilyl, tris(trimethylsilyl)silyl, (2-hydroxystyryl)dimethylsilyl, (2-hydroxystyryl)diisopropylsilyl, t-butylmethoxyphenylsilyl, t-butoxydiphenylsilyl, 1,1,3,3-tetraisopropyl-3-[2-(triphenylmethoxy)ethoxy]disiloxane-1-yl, and fluorous silyl. In the case of esters the protecting group for the OH can be selected from formate, benzoylformate, acetate, chloroacetate, dichloroacetate, trichloroacetate, trichloroacetamidate; trifluoroacetate, methoxyacetate, triphenylmethoxyacetate, phenoxyacetate, p-chlorophenoxyacetate, phenylacetate, diphenylacetate, 3-phenylpropionate, bisfluorous chain type propanoyl, 4-pentenoate, 4-oxopentanoate, 4,4-(ethylenedithio)pentanoate, 5[3-bis(4-methoxyphenyl)hydroxymethylphenoxy]levulinate, pivaloate, 1-adamantoate, crotonate, 4-methoxycrotonate, benzoate, p-phenylbenzoate, 2,4,6-trimethylbenzoate, 4-bromobenzoate, 2,5-difluorobenzoate, p-nitrobenzoate, picolinate, nicotinate, 2-(azidomethyl)benzoate, 4-azidobutyrate, (2-azidomethyl)phenylacetate, 2-{[(tritylthio)oxy]methyl}benzoate, 2-{[(4-methoxytritylthio)oxy]methyl}benzoate, 2-{[methyl(tritylthio)amino]methyl}benzoate, 2-{{[(4-methoxytrityl)thio]methylamino}-methyl}benzoate, 2-(allyloxy)phenylacetate, 2-(prenyloxymethyl)benzoate, 6-(levulinyloxymethyl)-3-methoxy-2-nitrobenzoate, 6-(levulinyloxymethyl)-3-methoxy-4-nitrobenzoate, 4-benzyloxybutyrate, 4-trialkylsilyloxybutyrate, 4-acetoxy-2,2-dimethylbutyrate, 2,2-dimethyl-4-pentenoate, 2-iodobenzoate, 4-nitro-4-methylpentanoate, o-(dibromomethyl)benzoate, 2-formylbenzenesulfonate, 4-(methylthiomethoxy)butyrate, 2-(methylthiomethoxymethyl)benzoate, 2-(chloroacetoxymethyl)benzoate, 2-[(2-chloroacetoxy)ethyl]benzoate, 2-[2-(benzyloxy)ethyl]benzoate, 2-[2-(4-methoxybenzyloxy)ethyl]benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, and 2-chlorobenzoate. In the case of sulfonates, sulfenates and sulfinates the protecting group for the OH can be selected from sulfate, allylsulfonate, methanesulfonate, benzylsulfonate, tosylate, 2-[(4-nitrophenyl)ethyl]sulfonate, 2-trifluoromethylbenzenesulfonate, 4-monomethoxytritylsulfenate, alkyl 2,4-dinitrophenylsulfenate, 2,2,5,5-tetramethylpyrrolidin-3-one-1-sulfinate, borate, and dimethylphosphinothiolyl. In the case of carbonates the protecting group for the OH can be selected from methyl carbonate, methoxymethyl carbonate, 9-fluorenylmethyl carbonate, ethyl carbonate, bromoethyl carbonate, 2-(methylthiomethoxy)ethyl carbonate, 2,2,2-trichloroethyl carbonate, 1,1-dimethyl-2,2,2-trichloroethyl carbonate, 2-(trimethylsilyl)ethyl carbonate, 2-[dimethyl(2-naphthylmethyl)silyl]ethyl carbonate, 2-(phenylsulfonyl)ethyl carbonate, 2-(triphenylphosphonio)ethyl carbonate, cis-[4-[[(methoxytrityl)sulfenyl]oxy]tetrahydrofuran-3-yl]oxy carbonate, isobutyl carbonate, t-butyl carbonate, vinyl carbonate, allyl carbonate, cinnamyl carbonate, propargyl carbonate, p-chlordphenyl carbonate, p-nitrophenyl carbonate, 4-ethoxy-1-naphthyl carbonate, 6-bromo-7-hydroxycoumarin-4-ylmethyl carbonate, benzyl carbonate, o-nitrobenzyl carbonate, p-nitrobenzyl carbonate, p-methoxybenzyl carbonate, 3,4-dimethoxybenzyl carbonate, anthraquinon-2-ylmethyl carbonate, 2-dansylethyl carbonate, 2-(4-nitrophenyl)ethyl carbonate, 2-(2,4-dinitrophenyl)ethyl carbonate, 2-(2-nitrophenyl)propyl carbonate, alkyl 2-(3,4-methylenedioxy-6-nitrophenyl)propyl carbonate, 2-cyano-1-phenylethyl carbonate, 2-(2-pyridyl)amino-1-phenylethyl carbonate, 2-[N-methyl-N-(2-pyridyl)]amino-1-phenylethyl carbonate, phenacyl carbonate, 3',5'-dimethoxybenzoin carbonate, methyl dithiocarbonate, and S-benzyl thiocarbonate. And in the case of carbamates the protecting group for the OH can be selected from dimethylthiocarbamate, N-phenylcarbamate, N-methyl-N-(o-nitrophenyl)carbamate. The mention of these groups should be not interpreted as a limitation of the scope of the invention, since they have been mentioned as a mere illustration of protecting groups for OH, but further groups having said function may be known by the skilled person in the art, and they are to be understood to be also encompassed by the present invention.

The term "pharmaceutically acceptable salts, prodrugs" refers to any pharmaceutically acceptable salt, ester, solvate, hydrate or any other compound which, upon administration to the patient is capable of providing (directly or indirectly) a compound as described herein. However, it will be appreciated that non-pharmaceutically acceptable salts also fall within the scope of the invention since those may be useful in the preparation of pharmaceutically acceptable salts. The preparation of salts and prodrugs can be carried out by methods known in the art.

For instance, pharmaceutically acceptable salts of compounds provided herein are synthesized from the parent compound, which contains a basic or acidic moiety, by conventional chemical methods. Generally, such salts are, for example, prepared by reacting the free acid or base forms of these compounds with a stoichiometric amount of the appropriate base or acid in water or in an organic solvent or in a mixture of the two. Generally, nonaqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, trifluoroacetate, maleate, fumarate, citrate, oxalate, succinate, tartrate, malate, mandelate, methanesulfonate and p-toluenesulfonate. Examples of the alkali addition salts include inorganic salts such as, for example, sodium, potassium, calcium and ammonium salts, and organic alkali salts such as, for example, ethylenediamine, ethanolamine, N,N-dialkylenethanolamine, triethanolamine and basic aminoacids salts.

The compounds of the invention may be in crystalline form either as free compounds or as solvates (e.g. hydrates) and it is intended that both forms are within the scope of the present invention. Methods of solvation are generally known within the art.

Any compound that is a prodrug of a compound of formula I is within the scope and spirit of the invention. The term "prodrug" as used in this application is defined here as meaning a chemical compound having undergone a chemical derivation such as substitution or addition of a further chemical group to change (for pharmaceutical use) any of its physicochemical properties, such as solubility or bioavailability, e.g. ester and ether derivatives of an active compound that yield the active compound per se after administration to a subject. Examples of well known methods of producing a prodrug of a given acting compound are known to those skilled in the art and can be found e.g. in Krogsgaard-Larsen et al., Textbook of Drugdesign and Discovery, Taylor & Francis (April 2002).

Any compound referred to herein is intended to represent such specific compound as well as certain variations or forms. In particular, compounds referred to herein may have asymmetric centres and therefore exist in different enantiomeric forms. All optical isomers and stereoisomers of the compounds referred to herein, and mixtures thereof, are considered within the scope of the present invention. Thus any given compound referred to herein is intended to represent any one of a racemate, one or more enantiomeric forms, one or more diastereomeric forms, one or more atropisomeric forms, and mixtures thereof. Particularly, the compounds of the present invention represented by the above described formula I may include enantiomers depending on their asymmetry or diastereoisomers. Stereoisomerism about the double bond is also possible, therefore in some cases the molecule could exist as (E)-isomer or (Z)-isomer. If the molecule contains several double bonds, each double bond will have its own stereoisomerism, that could be the same or different than the stereoisomerism of the other double bonds of the molecule. The single isomers and mixtures of isomers fall within the scope of the present invention.

Furthermore, compounds referred to herein may exist as geometric isomers (i.e., cis and trans isomers), as tautomers, or as atropisomers. Specifically, the term tautomer refers to one of two or more structural isomers of a compound, that exist in equilibrium and are readily converted from one isomeric form to another. Common tautomeric pairs are amine-imine, amide-imide, keto-enol, lactam-lactim, etc. Additionally, any compound referred to herein is intended to represent hydrates, solvates, and polymorphs, and mixtures thereof when such forms exist in the medium. In addition, compounds referred to herein may exist in isotopically-labelled forms. All geometric isomers, tautomers, atropisomers, hydrates, solvates, polymorphs, and isotopically labelled forms of the compounds referred to herein, and mixtures thereof, are considered within the scope of the present invention.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skilled in the art, including equivalents and approximations due to the experimental and/or measurement conditions for such given value.

In compounds of general formula I, particularly preferred Y is —$CHR_{ay}$—, —$CR_{ay}$=$CR_{by}$—, and —$CHR_{ay}$—$CR_{by}$=$CR_{cy}$—, wherein $R_{ay}$, $R_{by}$, and $R_{cy}$ are as defined before.

Particularly preferred $R_{ay}$, $R_{by}$, and $R_{cy}$ are hydrogen and substituted or unsubstituted $C_1$-$C_{12}$ alkyl. More preferred $R_{ay}$, $R_{by}$, and $R_{cy}$ are hydrogen and substituted or unsubstituted $C_1$-$C_6$ alkyl, and even more preferred is hydrogen, substituted or unsubstituted methyl, substituted or unsubstituted ethyl, substituted or unsubstituted propyl, substituted or unsubstituted isopropyl, and substituted or unsubstituted butyl, including substituted or unsubstituted tert-butyl, substituted or unsubstituted isobutyl, and substituted or unsubstituted sec-butyl. Preferred substituents of said groups are OR', =O, SR', SOR', $SO_2R'$, $NO_2$, NHR', NR'R', =N—R', NHCOR', $N(COR')_2$, $NHSO_2R'$, NR'C(=NR')NR'R', CN, halogen, COR', COOR', OCOR', OCONHR', OCONR'R', CONHR', CONR'R', protected OH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group, wherein each of the R' groups is independently selected from the group consisting of hydrogen, OH, $NO_2$, $NH_2$, SH, CN, halogen, COH, COalkyl, COOH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group. Where such groups are themselves substituted, the substituents may be chosen from the foregoing list. Even more preferred substituents of the above mentioned groups are OH, $SCH_3$, SH, $NH_2$, $NHC(=NH)NH_2$, $CONH_2$, COOH, phenyl, p-, m- or o-hydroxyphenyl, indolyl, including 1-, 2-, and 3-indolyl, and imidazolyl, including 4- and 5-imidazolyl. Hydrogen and methyl are the most preferred $R_{ay}$, $R_{by}$, and $R_{cy}$ groups. Specifically, when Y is —$CHR_{ay}$— then particularly preferred $R_{ay}$ is methyl, when Y is —$CR_{ay}$=$CR_{by}$— then particularly preferred $R_{ay}$ is hydrogen and particularly preferred $R_{by}$ is methyl, and when Y is —$CHR_{ay}$—$CR_{by}$=$CR_{cy}$— then particularly preferred $R_{ay}$ is hydrogen or methyl, particular preferred $R_{by}$ is hydrogen, and particularly preferred $R_{cy}$ is methyl.

Particularly preferred $R_1$, $R_2$, $R_3$, $R_4$, and $R_5$ are hydrogen and substituted or unsubstituted $C_1$-$C_{12}$ alkyl. More preferred $R_1$, $R_2$, $R_3$, $R_4$, and $R_5$ are hydrogen and substituted or unsubstituted $C_1$-$C_6$ alkyl, and even more preferred is hydrogen, substituted or unsubstituted methyl, substituted or unsubstituted ethyl, substituted or unsubstituted propyl, substituted or unsubstituted isopropyl and substituted or unsubstituted butyl, including substituted or unsubstituted tert-butyl, substituted or unsubstituted isobutyl and substituted or unsubstituted sec-butyl. Preferred substituents of said groups are OR', =O, SR', SOR', $SO_2R'$, $NO_2$, NHR', NR'R', =N—R', NHCOR', $N(COR')_2$, $NHSO_2R'$, NR'C(=NR')NR'R', CN, halogen, COR', COOR', OCOR', OCONHR', OCONR'R', CONHR', CONR'R', protected OH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group, wherein each of the R' groups is independently selected from the group consisting of hydrogen, OH, $NO_2$, $NH_2$, SH, CN, halogen, COH, COalkyl, COOH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group. Where such groups are themselves substituted, the substituents may be chosen from the foregoing list. Even more preferred substituents of the above mentioned groups are OH, $SCH_3$, SH, $NH_2$, $NHC(=NH)NH_2$, $CONH_2$, COOH, phenyl, p-, m- or o-hydroxyphenyl, indolyl, including 1-, 2-, and 3-indolyl, and imidazolyl, including 4- and 5-imidazolyl. Hydrogen, methyl, isopropyl, tert-butyl, and benzyl are the most preferred $R_1$, $R_2$, $R_3$, $R_4$, and $R_5$ groups. Specifically, particularly preferred $R_1$, $R_2$, $R_3$, and $R_4$ are hydrogen. And particularly preferred $R_5$ are methyl, isopropyl, and tert-butyl.

Particularly preferred W is $NR_7$ wherein $R_7$ is as defined before. Particularly preferred $R_7$ is hydrogen and substituted or unsubstituted $C_1$-$C_{12}$ alkyl. More preferred $R_7$ is hydrogen and substituted or unsubstituted $C_1$-$C_6$ alkyl; and even more preferred is hydrogen, methyl, ethyl, propyl, isopropyl and butyl, including tert-butyl. Hydrogen is the most preferred.

In another embodiment, it is particularly preferred that $R_7$ and $R_5$ together with the corresponding N atom and C atom to which they are attached form a substituted or unsubstituted heterocyclic group. In this regard, preferred heterocyclic group is a heteroalicyclic group containing one, two or three heteroatoms selected from N, O or S atoms, most preferably one N atom, and having from 5 to about 10 ring atoms, most preferably 5, 6 or 7 ring atoms. A pyrrolidine group is the most preferred.

Particularly preferred $R_6$ is $NR_8R_9$ and $OR_{10}$ wherein $R_8$, $R_9$, and $R_{10}$ are as defined before, and even more preferred $R_6$ is $NR_8R_9$.

Particularly preferred $R_8$ is hydrogen.

Particularly preferred $R_9$ is hydrogen, substituted or unsubstituted $C_2$-$C_{12}$ alkenyl, substituted or unsubstituted $C_2$-$C_{12}$ alkynyl, and substituted or unsubstituted $C_4$-$C_{12}$ alkenynyl. The preferred substituted alkenyl, substituted alkynyl and substituted alkenynyl may present not only one but two or more substituents. More preferred alkenyl groups are those having from 6 to about 10 carbon atoms; and even more preferably 7, 8 or 9 carbon atoms. Octa-1,6-dienyl, octa-1,5-dienyl, octa-1,4-dienyl, octa-1,3-dienyl, nona-1,7-dienyl, nona-1,6-dienyl, nona-1,5-dienyl, nona-1,4-dienyl, nona-1,3-dienyl, hepta-1,5-dienyl, hepta-1,4-dienyl, hepta-1,3-dienyl are the most preferred alkenyl groups. On the other hand, more preferred alkynyl groups are those having from 6 to about 10 carbon atoms; and even more preferably 7, 8 or 9 carbon atoms. Oct-7-ynyl, oct-6-ynyl, oct-5-ynyl, oct-4-ynyl, oct-3-ynyl, oct-2-ynyl, oct-1-ynyl, non-8-ynyl, non-7-ynyl, non-6-ynyl, non-5-ynyl, non-4-ynyl, non-3-ynyl, non-2-ynyl, non-1-ynyl, hept-6-ynyl, hept-5-ynyl, hept-4-ynyl, hept-3-ynyl, hept-2-ynyl, and hept-1-ynyl are the most preferred alkynyl groups. On the other hand, more preferred alkenynyl groups are those having from 6 to about 10 carbon atoms; and even more preferably 7, 8 or 9 carbon atoms. Oct-1-en-7-ynyl, oct-1-en-6-ynyl, oct-1-en-5-ynyl, oct-1-en-4-ynyl, oct-1-en-3-ynyl, non-1-en-8-ynyl, non-1-en-7-ynyl, non-1-en-6-ynyl, non-1-en-5-ynyl, non-1-en-4-ynyl, non-1-en-3-ynyl, hept-1-en-6-ynyl, hept-1-en-5-ynyl, hept-1-en-4-ynyl, and hept-1-en-3-ynyl, are the most preferred alkenynyl groups. Preferred substituents for said alkenyl, alkynyl and alkenynyl groups are OR', =O, SR', SOR', $SO_2R'$, $NO_2$, NHR', NR'R', =N—R', NHCOR', $N(COR')_2$, $NHSO_2R'$, NR'C(=NR') NR'R', CN, halogen, COR', COOR', OCOR', OCONHR', OCONR'R', CONHR', CONR'R', protected OH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group, wherein each of the R' groups is independently selected from the group consisting of hydrogen, OH, $NO_2$, $NH_2$, SH, CN, halogen, COH, COalkyl, COOH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group. Where such groups are themselves substituted, the substituents may be chosen from the foregoing list. More preferred substituents for the above mentioned alkenyl, alkynyl and alkenynyl groups are halogen, OR', =O, OCOR', OCONHR', OCONR'R', CONHR', CONR'R', and protected OH, wherein each of the R' groups is preferably selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, and substituted or unsubstituted aryl. Even more preferred substituents for these alkenyl, alkynyl and alkenynyl groups are halogen, OR', =O, OCONHR', OCONR'R', CONHR', CONR'R', and protected OH wherein the protecting group for the OH is preferably selected from trimethylsilyl, triethylsilyl, triisopropylsilyl, dimethylisopropylsilyl, diethylisopropylsilyl, dimethylhexylsylil, 2-norbornyldimethylsilyl, t-butyldimethylsilyl, t-butyldiphenylsilyl, tribenzylsilyl, tri-p-xylylsilyl, triphenylsilyl, diphenylmethylsilyl, di-t-butylmethylsilyl, bis(t-butyl)-1-pyrenylmethoxysilyl, tris(trimethylsilyl)silyl, (2-hydroxystyryl)dimethylsilyl, (2-hydroxystyryl)diisopropylsilyl, t-butylmethoxyphenylsilyl, t-butoxydiphenylsilyl, 1,1,3,3-tetraisopropyl-3-[2-(triphenylmethoxy)ethoxy]disiloxane-1-yl, and fluorous silyl, and wherein each of the R' groups is more preferably selected from hydrogen, unsubstituted $C_1$-$C_6$ alkyl, and substituted or unsubstituted aryl. Cl, OH, =O, OCONH$_2$, OCONHPhenyl, and protected OH wherein the protecting group for the OH is preferably selected from trimethylsilyl, triethylsilyl, triisopropylsilyl, dimethylisopropylsilyl, diethylisopropylsilyl, dimethylhexylsylil, 2-norbornyldimethylsilyl, t-butyldimethylsilyl, t-butyldiphenylsilyl, tribenzylsilyl, tri-p-xylylsilyl, triphenylsilyl, diphenylmethylsilyl, di-t-butylmethylsilyl, bis(t-butyl)-1-pyrenylmethoxysilyl, tris(trimethylsilyl) silyl, (2-hydroxystyryl)dimethylsilyl, (2-hydroxystyryl) diisopropylsilyl, t-butylmethoxyphenylsilyl, t-butoxydiphenylsilyl, 1,1,3,3-tetraisopropyl-3-[2-(triphenylmethoxy)ethoxy]disiloxane-1-yl, and fluorous silyl, are the most preferred substituents for these alkenyl, alkynyl and alkenynyl groups.

Particularly preferred $R_{11}$, $R_{12}$, $R_{13}$, $R_{14}$, and $R_{15}$ are hydrogen, $OR_a$, $OCOR_a$, and $OSiR_aR_bR_c$, wherein $R_a$, $R_b$, and $R_c$ are as defined above. Specifically, particular preferred $R_{11}$, $R_{14}$, and $R_{15}$ are hydrogen, particular preferred $R_{12}$ is hydrogen and $OR_a$, and particular preferred $R_{13}$ is hydrogen, $OR_a$, and $OSiR_aR_bR_c$. Particular preferred $R_a$, $R_b$, and $R_c$ are hydrogen and substituted or unsubstituted $C_1$-$C_{12}$ alkyl. Even more preferred $R_a$, $R_b$, and $R_c$ are hydrogen and substituted or unsubstituted $C_1$-$C_6$ alkyl; and even more preferred are hydrogen, methyl, ethyl, propyl, isopropyl and butyl, including tert-butyl, being hydrogen, methyl, and tert-butyl the most preferred.

Particularly preferred is the presence of one additional bond between the C atoms to which $R_1$ and $R_2$ are attached, and the presence of one or two additional bonds between the C atoms to which $R_3$ and $R_4$ are attached. In addition, the stereochemistry of each double bond may exist as (E) or (Z). The single isomers and mixtures of the isomers fall within the scope of the present invention.

More particularly, preferred compounds of general formula I are those also having general formula IA or pharmaceutically acceptable salts, tautomers, prodrugs or stereoisomers thereof

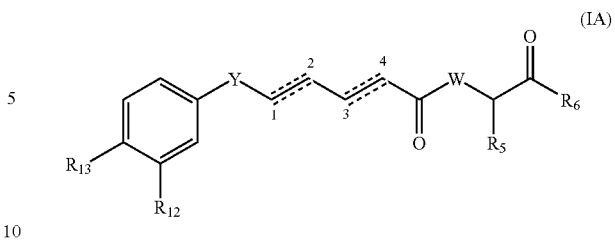

(IA)

wherein Y is selected from —CHR$_{ay}$—, —CHR$_{ay}$—CHR$_{by}$—, —CR$_{ay}$=CR$_{by}$—, —C≡C—, —CHR$_{ay}$—CHR$_{by}$—CHR$_{cy}$—, —CHR$_{ay}$—CR$_{by}$=CR$_{cy}$—, and —CHR$_{ay}$—C≡C—;

each $R_{ay}$, $R_{by}$, and $R_{cy}$ is independently selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl; $R_5$ is selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

$R_6$ is selected from $NR_8R_9$, and $OR_{10}$;

W is selected from O and $NR_7$;

$R_7$ is selected from hydrogen, $COR_a$, $COOR_a$, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl, or $R_7$ and $R_5$ together with the corresponding N atom and C atom to which they are attached may form a substituted or unsubstituted heterocyclic group;

each $R_8$ and $R_9$ are independently selected from hydrogen, $COR_a$, $COOR_a$, substituted or unsubstituted $C_2$-$C_{12}$ alkenyl, substituted or unsubstituted $C_2$-$C_{12}$ alkynyl, and substituted or unsubstituted $C_4$-$C_{12}$ alkenynyl;

$R_{10}$ is selected from hydrogen, substituted or unsubstituted $C_2$-$C_{12}$ alkenyl, and substituted or unsubstituted $C_2$-$C_{12}$ alkynyl;

each $R_{12}$ and $R_{13}$ are independently selected from hydrogen, halogen, $OR_a$, $COR_a$, $COOR_a$, $OCOR_a$, $OCOOR_a$, $OCONR_aR_b$, $CONR_aR_b$, $OS(O)R_a$, $OSO_2R_a$, $OP(O)(R_a)OR_b$, $OSiR_aR_bR_c$, $NR_aR_b$, $NR_aCOR_b$, $NR_aCONR_aR_b$, $NR_aS(O)R_b$, $NR_aSO_2R_b$, $NR_aC(=NR_a)NR_aR_b$, $SR_a$, $S(O)R_a$, $SO_2R_a$, $S(O)NR_aR_b$, $SO_2NR_aR_b$, $S(O)OR_a$, $SO_2OR_a$, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

each $R_a$, $R_b$, and $R_c$ are independently selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group; and each dotted line represents an optional additional bond with the proviso that one or more additional bonds are present.

In compounds of general formula IA, particularly preferred Y is —CHR$_{ay}$—, —CR$_{ay}$=CR$_{by}$—, and —CHR$_{ay}$—CR$_{by}$=CR$_{cy}$—, $R_{ay}$, $R_{by}$, and $R_{cy}$ are as defined before.

Particularly preferred $R_{ay}$, $R_{by}$, and $R_{cy}$ are hydrogen and substituted or unsubstituted $C_1$-$C_{12}$ alkyl. More preferred $R_{ay}$, $R_{by}$, and $R_{cy}$ are hydrogen and substituted or unsubstituted $C_1$-$C_6$ alkyl, and even more preferred is hydrogen, substituted or unsubstituted methyl, substituted or unsubstituted ethyl, substituted or unsubstituted propyl, substituted or unsubstituted isopropyl, and substituted or unsubstituted butyl, including substituted or unsubstituted tert-butyl, substituted or unsubstituted isobutyl, and substituted or unsubstituted sec-butyl. Preferred substituents of said groups are OR', =O, SR', SOR', SO$_2$R', NO$_2$, NHR', NR'R', =N—R', NHCOR', N(COR')$_2$, NHSO$_2$R', NR'C(=NR')NR'R', CN, halogen, COR', COOR', OCOR', OCONHR', OCONR'R', CONHR', CONR'R', protected OH, substituted or unsubstituted C$_1$-C$_{12}$ alkyl, substituted or unsubstituted C$_2$-C$_{12}$ alkenyl, substituted or unsubstituted C$_2$-C$_{12}$ alkynyl, substituted or unsubstituted aryl, and substituted or unsubstituted heterocyclic group, wherein each of the R' groups is independently selected from the group consisting of hydrogen, OH, NO$_2$, NH$_2$, SH, CN, halogen, COH, COalkyl, COOH, substituted or unsubstituted C$_1$-C$_{12}$ alkyl, substituted or unsubstituted C$_2$-C$_{12}$ alkenyl, substituted or unsubstituted C$_2$-C$_{12}$ alkynyl, substituted or unsubstituted aryl, and substituted or unsubstituted heterocyclic group. Where such groups are themselves substituted, the substituents may be chosen from the foregoing list. Even more preferred substituents of the above mentioned groups are OH, SCH$_3$, SH, NH$_2$, NHC(=NH)NH$_2$, CONH$_2$, COOH, phenyl, p-, m- or o-hydroxyphenyl, indolyl, including 1-, 2-, and 3-indolyl, and imidazolyl, including 4- and 5-imidazolyl. Hydrogen and methyl are the most preferred R$_{ay}$, R$_{by}$, and R$_{cy}$ groups. Specifically, when Y is —CHR$_{ay}$— then particularly preferred R$_{ay}$ is methyl, when Y is —CR$_{ay}$=CR$_{by}$— then particularly preferred R$_{ay}$ is hydrogen and particularly preferred R$_{by}$ is methyl, and when Y is —CHR$_{ay}$—CR$_{by}$=CR$_{cy}$— then particularly preferred R$_{ay}$ is hydrogen or methyl, particular preferred R$_{by}$ is hydrogen, and particularly preferred R$_{cy}$ is methyl.

Particularly preferred R$_s$ is hydrogen and substituted or unsubstituted C$_1$-C$_{12}$ alkyl. More preferred R$_5$ is hydrogen and substituted or unsubstituted C$_1$-C$_6$ alkyl, and even more preferred is hydrogen, substituted or unsubstituted methyl, substituted or unsubstituted ethyl, substituted or unsubstituted propyl, substituted or unsubstituted isopropyl and substituted or unsubstituted butyl, including substituted or unsubstituted tert-butyl, substituted or unsubstituted isobutyl and substituted or unsubstituted sec-butyl. Preferred substituents of said groups are OR', =O, SR', SOR', SO$_2$R', NO$_2$, NHR', NR'R', =N—R', NHCOR', N(COR')$_2$, NHSO$_2$R', NR'C(=NR')NR'R', CN, halogen, COR', COOR', OCOR', OCONHR', OCONR'R', CONHR', CONR'R', protected OH, substituted or unsubstituted C$_1$-C$_{12}$ alkyl, substituted or unsubstituted C$_2$-C$_{12}$ alkenyl, substituted or unsubstituted C$_2$-C$_{12}$ alkynyl, substituted or unsubstituted aryl, and substituted or unsubstituted heterocyclic group, wherein each of the R' groups is independently selected from the group consisting of hydrogen, OH, NO$_2$, NH$_2$, SH, CN, halogen, COH, COalkyl, COOH, substituted or unsubstituted C$_1$-C$_{12}$ alkyl, substituted or unsubstituted C$_2$-C$_{12}$ alkenyl, substituted or unsubstituted C$_2$-C$_{12}$ alkynyl, substituted or unsubstituted aryl, and substituted or unsubstituted heterocyclic group. Where such groups are themselves substituted, the substituents may be chosen from the foregoing list. Even more preferred substituents of the above mentioned groups are OH, SCH$_3$, SH, NH$_2$, NHC(=NH)NH$_2$, CONH$_2$, COOH, phenyl, p-, m- or o-hydroxyphenyl, indolyl, including 1-, 2-, and 3-indolyl, and imidazolyl, including 4- and 5-imidazolyl. Hydrogen, methyl, isopropyl, tert-butyl, and benzyl are the most preferred R$_5$ groups, and even most preferred methyl, isopropyl, and tert-butyl.

Particularly preferred W is NR$_7$ wherein R$_7$ is as defined before. Particularly preferred R$_7$ is hydrogen and substituted or unsubstituted C$_1$-C$_{12}$ alkyl. More preferred R$_7$ is hydrogen and substituted or unsubstituted C$_1$-C$_6$ alkyl; and even more preferred is hydrogen, methyl, ethyl, propyl, isopropyl and butyl, including tert-butyl. Hydrogen is the most preferred.

In another embodiment, it is particularly preferred that R$_7$ and R$_5$ together with the corresponding N atom and C atom to which they are attached form a substituted or unsubstituted heterocyclic group. In this regard, preferred heterocyclic group is a heteroalicyclic group containing one, two or three heteroatoms selected from N, O or S atoms, most preferably one N atom, and having from 5 to about 10 ring atoms, most preferably 5, 6 or 7 ring atoms. A pyrrolidine group is the most preferred.

Particularly preferred R$_6$ is NR$_8$R$_9$ and OR$_{10}$ wherein R$_8$, R$_9$, and R$_{10}$ are as defined before, and even more preferred R$_6$ is NR$_8$R$_9$.

Particularly preferred R$_8$ is hydrogen.

Particularly preferred R$_9$ is hydrogen, substituted or unsubstituted C$_2$-C$_{12}$ alkenyl, substituted or unsubstituted C$_2$-C$_{12}$ alkynyl, and substituted or unsubstituted C$_4$-C$_{12}$ alkenynyl. The preferred substituted alkenyl, substituted alkynyl, and substituted alkenynyl may present not only one but two or more substituents. More preferred alkenyl groups are those having from 6 to about 10 carbon atoms; and even more preferably 7, 8 or 9 carbon atoms. Octa-1,6-dienyl, octa-1,5-dienyl, octa-1,4-dienyl, octa-1,3-dienyl, nona-1,7-dienyl, nona-1,6-dienyl, nona-1,5-dienyl, nona-1,4-dienyl, nona-1,3-dienyl, hepta-1,5-dienyl, hepta-1,4-dienyl, hepta-1,3-dienyl are the most preferred alkenyl groups. On the other hand, more preferred alkynyl groups are those having from 6 to about 10 carbon atoms; and even more preferably 7, 8 or 9 carbon atoms. Oct-7-ynyl, oct-6-ynyl, oct-5-ynyl, oct-4-ynyl, oct-3-ynyl, oct-2-ynyl, oct-1-ynyl, non-8-ynyl, non-7-ynyl, non-6-ynyl, non-5-ynyl, non-4-ynyl, non-3-ynyl, non-2-ynyl, non-1-ynyl, hept-6-ynyl, hept-5-ynyl, hept-4-ynyl, hept-3-ynyl, hept-2-ynyl, and hept-1-ynyl are the most preferred alkynyl groups. On the other hand, more preferred alkenynyl groups are those having from 6 to about 10 carbon atoms; and even more preferably 7, 8 or 9 carbon atoms. Oct-1-en-7-ynyl, oct-1-en-6-ynyl, oct-1-en-5-ynyl, oct-1-en-4-ynyl, oct-1-en-3-ynyl, non-1-en-8-ynyl, non-1-en-7-ynyl, non-1-en-6-ynyl, non-1-en-5-ynyl, non-1-en-4-ynyl, non-1-en-3-ynyl, hept-1-en-6-ynyl, hept-1-en-5-ynyl, hept-1-en-4-ynyl, and hept-1-en-3-ynyl, are the most preferred alkenynyl groups. Preferred substituents for said alkenyl, alkynyl and alkenynyl groups are OR', =O, SR', SOR', SO$_2$R', NO$_2$, NHR', NR'R', =N—R', NHCOR', N(COR')$_2$, NHSO$_2$R', NR'C(=NR') NR'R', CN, halogen, COR', COOR', OCOR', OCONHR', OCONR'R', CONHR', CONR'R', protected OH, substituted or unsubstituted C$_1$-C$_{12}$ alkyl, substituted or unsubstituted C$_2$-C$_{12}$ alkenyl, substituted or unsubstituted C$_2$-C$_{12}$ alkynyl, substituted or unsubstituted aryl, and substituted or unsubstituted heterocyclic group, wherein each of the R' groups is independently selected from the group consisting of hydrogen, OH, NO$_2$, NH$_2$, SH, CN, halogen, COH, COalkyl, COOH, substituted or unsubstituted C$_1$-C$_{12}$ alkyl, substituted or unsubstituted C$_2$-C$_{12}$ alkenyl, substituted or unsubstituted C$_2$-C$_{12}$ alkynyl, substituted or unsubstituted aryl, and substituted or unsubstituted heterocyclic group. Where such groups are themselves substituted, the substituents may be chosen from the foregoing list. More preferred substituents for the above mentioned alkenyl, alkynyl and alkenynyl groups are halogen, OR', =O, OCOR', OCONHR', OCONR'R', CONHR', CONR'R', and protected OH, wherein each of the R' groups is preferably selected from hydrogen, substituted or unsubstituted C$_1$-C$_{12}$ alkyl, substituted or unsubstituted C$_2$-C$_{12}$ alkenyl, substituted or unsubstituted C$_2$-C$_{12}$ alkynyl, and substituted or unsubstituted aryl. Even more preferred substituents for these alkenyl, alkynyl and alkenynyl groups are halogen, OR', =O, OCONHR', OCONR'R', CONHR', CONR'R', and protected OH wherein the protecting group for the OH is preferably selected from trimethylsilyl, triethylsilyl, triisopropylsilyl, dimethylisopropylsilyl, diethylisopropylsilyl, dimethylhexylsylil, 2-norbornyldimethylsilyl, t-butyldimethylsilyl, t-butyldiphenylsilyl, tribenzylsilyl, tri-p-xylylsilyl, triphenylsilyl, diphenylmethylsilyl, di-t-butylmethylsilyl, bis(t-butyl)-1-pyrenylmethoxysilyl, tris(trimethylsilyl)silyl, (2-hydroxystyryl)dimethylsilyl, (2-hydroxystyryl)diisopropylsilyl, t-butylmethoxyphenylsilyl, t-butoxydiphenylsilyl, 1,1,3,3-tetraisopropyl-3-[2-(triphenylmethoxy)ethoxy]disiloxane-1-yl, and fluorous silyl, and wherein each of the R' groups is more preferably selected from hydrogen, unsubstituted $C_1$-$C_6$ alkyl, and substituted or unsubstituted aryl. Cl, OH, =O, OCONH$_2$, OCONHPhenyl, and protected OH wherein the protecting group for the OH is preferably selected from trimethylsilyl, triethylsilyl, triisopropylsilyl, dimethylisopropylsilyl, diethylisopropylsilyl, dimethylhexylsylil, 2-norbornyldimethylsilyl, t-butyldimethylsilyl, t-butyldiphenylsilyl, tribenzylsilyl, tri-p-xylylsilyl, triphenylsilyl, diphenylmethylsilyl, di-t-butylmethylsilyl, bis(t-butyl)-1-pyrenylmethoxysilyl, tris(trimethylsilyl)silyl, (2-hydroxystyryl)dimethylsilyl, (2-hydroxystyryl)diisopropylsilyl, t-butylmethoxyphenylsilyl, t-butoxydiphenylsilyl, 1,1,3,3-tetraisopropyl-3-[2-(triphenylmethoxy)ethoxy]disiloxane-1-yl, and fluorous silyl, are the most preferred substituents for these alkenyl, alkynyl and alkenynyl groups.

Particularly preferred $R_{12}$ and $R_{13}$ are hydrogen, $OR_a$, $OCOR_a$, and $OSiR_aR_bR_c$, wherein $R_a$, $R_b$, and $R_c$ are as defined above. Even more preferred $R_{12}$ is hydrogen and $OR_a$, and more preferred $R_{13}$ is hydrogen, $OR_a$, and $OSiR_aR_bR_c$. Particular preferred $R_a$, $R_b$, and $R_c$ are hydrogen and substituted or unsubstituted $C_1$-$C_{12}$ alkyl. Even more preferred $R_a$, $R_b$, and $R_c$ are hydrogen and substituted or unsubstituted $C_1$-$C_6$ alkyl; and even more preferred are hydrogen, methyl, ethyl, propyl, isopropyl and butyl, including tert-butyl, being hydrogen, methyl, and tert-butyl the most preferred.

Particularly preferred is the presence of one additional bond between $C_1$ and $C_2$, and/or the presence of one or two additional bonds between $C_3$ and $C_4$. In addition, the stereochemistry of each double bond may exist as (E) or (Z). The single isomers and mixtures of the isomers fall within the scope of the present invention.

The compounds of the invention can be obtained synthetically by joining different fragments as indicated in the Scheme A.

where $R_1$, $R_2$, $R_3$, $R_4$, $R_5$, $R_6$, $R_{11}$, $R_{12}$, $R_{13}$, $R_{14}$, $R_{15}$, Y and W are the desired groups or an appropriate protecting group as needed, and J, K, L, and M are appropriate reacting or leaving groups.

The compounds of the invention can be obtained by either of the following strategies:

1) Fragments A and B can be coupled following standard procedures in organic chemistry (i.e. Bodanszky M and Bodanszky A, The Practice of Peptide Synthesis, Springer-Verlag, 1993).

2) Fragments C and D can be coupled following standard procedures of organometallic chemistry (i.e. R. B. Crabtree, "The Organometallic Chemistry of the Transition Metals", 2nd Ed., Wiley, Nueva York, 1994).

Fragments A, B, C and D can be independently prepared following standard procedures in organic synthesis.

Deprotection of the protecting groups can be achieved according to known procedures in organic synthesis (Greene and Wuts, Protective Groups in Organic Synthesis, 3$^{rd}$ ed., Wiley-Interscience; Burke and Danheiser, Handbook of Reagents for Organic Synthesis: Oxidizing and Reducing Agents, Wiley; Pla D et al. J. Org. Chem. 2005, 70, 8231).

When necessary, appropriate protecting groups can be used on the substituents to ensure that reactive groups are not affected. The synthesis can be designed to employ precursor substituents which can be converted at the appropriate stage to a desired substituent. Saturation or unsaturation in the ring-structure can be introduced or removed as part of the synthesis. Starting materials and reagents can be modified as desired to ensure synthesis of the intended compound. In addition, analogues can also be synthesized from the obtained compounds by usual procedures in synthetic organic chemistry which are known by a person skilled in the art.

The synthetic routes above mentioned can be modified as desired to give stereospecific compounds as well as mixtures of stereoisomers. It is possible to synthesize specific stereoisomers or specific mixtures by various methods including the use of stereospecific reagents or by introducing chiral centers into the compounds during the synthesis. It is possible to introduce one or more stereocenters during synthesis and also invert existing stereocenters. In addition, it is possible to Scheme A

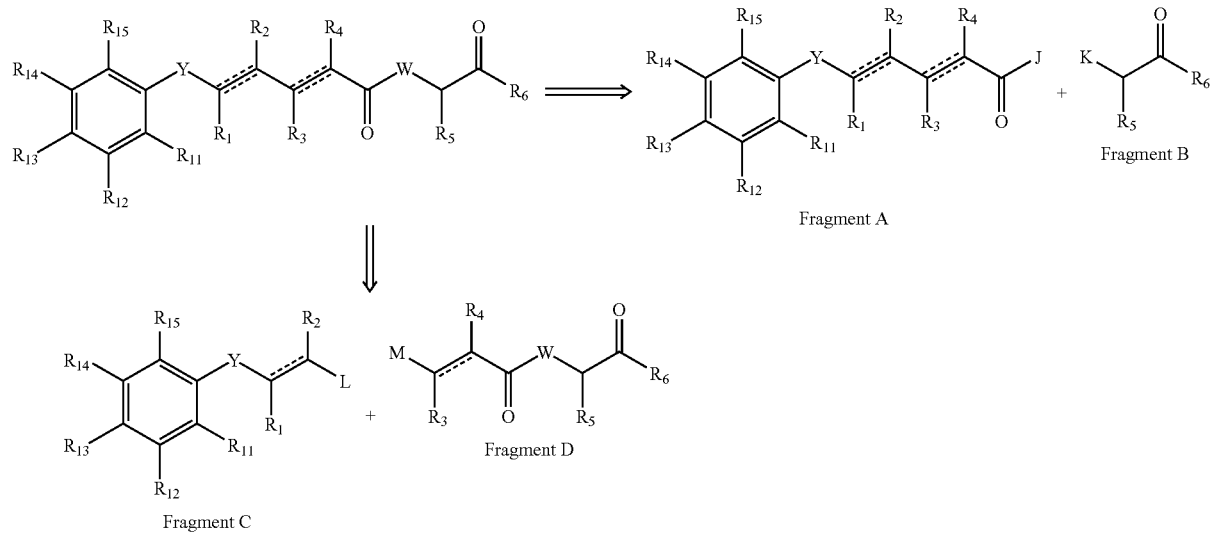

Fragment A

Fragment B

Fragment C

Fragment D separate stereoisomers once the compound has been synthesized by standard resolution techniques known to the skilled reader.

An important feature of the above described compounds of formula I is their bioactivity and in particular their cytotoxic activity.

With this invention we provide novel pharmaceutical compositions of compounds of general formula I that possess cytotoxic activity and their use as antitumor agents. Thus the present invention further provides pharmaceutical compositions comprising a compound of this invention, a pharmaceutically acceptable salt, tautomer, prodrug or stereoisomer thereof with a pharmaceutically acceptable carrier.

The term "carrier" refers to a diluent, adjuvant, excipient or vehicle with which the active ingredient is administered. Suitable pharmaceutical carriers are described in "Remington's Pharmaceutical Sciences" by E. W. Martin, 1995.

Examples of pharmaceutical compositions include any solid (tablets, pills, capsules, granules, etc.) or liquid (solutions, suspensions or emulsions) compositions for oral, topical or parenteral administration.

Administration of the compounds or compositions of the present invention may be by any suitable method, such as intravenous infusion, oral preparations, and intraperitoneal and intravenous administration. We prefer that infusion times of up to 24 hours are used, more preferably 1-12 hours, with 1-6 hours most preferred. Short infusion times which allow treatment to be carried out without an overnight stay in hospital are especially desirable. However, infusion may be 12 to 24 hours or even longer if required. Infusion may be carried out at suitable intervals of say 1 to 4 weeks. Pharmaceutical compositions containing compounds of the invention may be delivered by liposome or nanosphere encapsulation, in sustained release formulations or by other standard delivery means.

The correct dosage of the compounds will vary according to the particular formulation, the mode of application, and the particular situs, host and tumour being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

The compounds and compositions of this invention may be used with other drugs to provide a combination therapy. The other drugs may form part of the same composition, or be provided as a separate composition for administration at the same time or at different time.

Antitumoral activities of these compounds include, but are not limited, lung cancer, colon cancer, and breast cancer.

EXAMPLES

Example 1

Synthesis of Fragments 12 and 13

Scheme 1 provides an example of the synthesis of fragments 12 and 13.

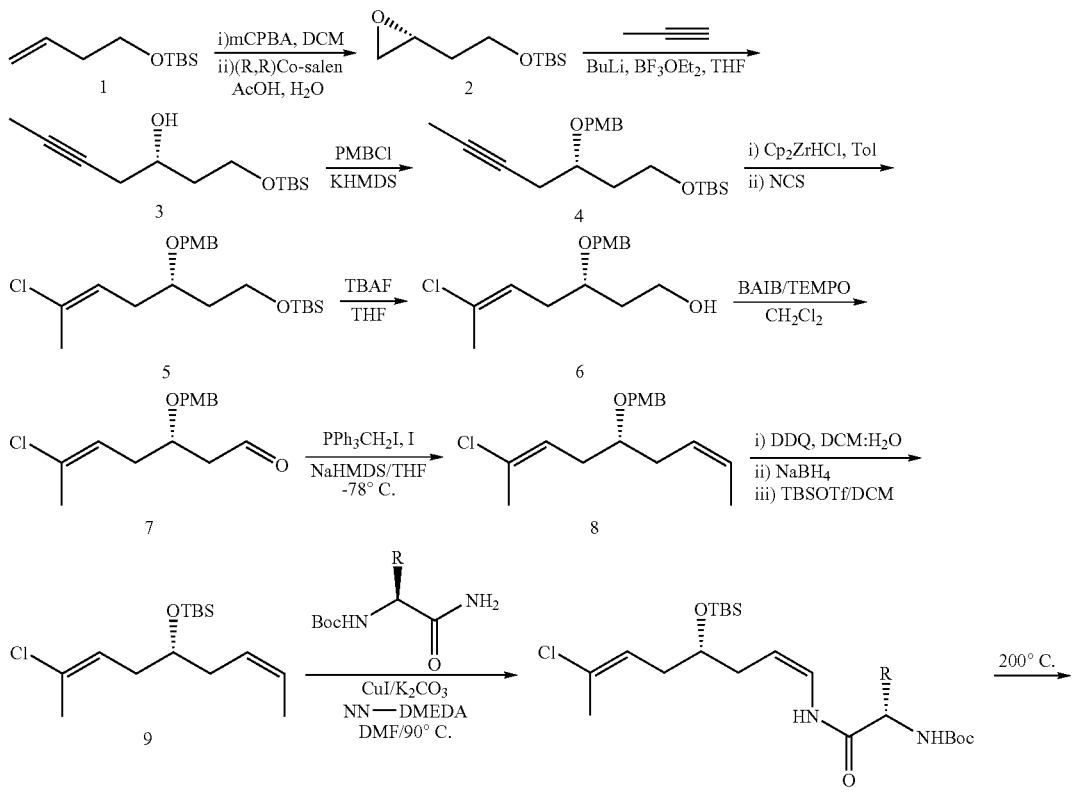

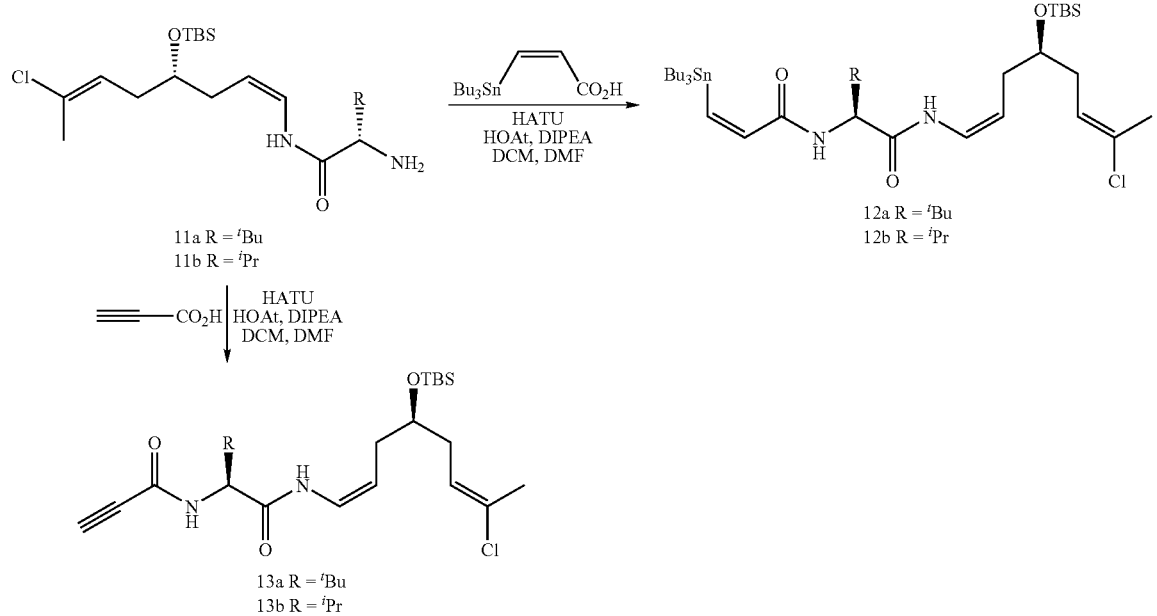

11a R = $^t$Bu
11b R = $^i$Pr

12a R = $^t$Bu
12b R = $^i$Pr

13a R = $^t$Bu
13b R = $^i$Pr

Synthesis of Intermediate 2

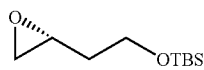

To a solution of intermediate 1 (72.3 g, 0.39 mol) in anhydrous DCM (918 mL) at room temperature 3-Chloroperbenzoic acid (m-CPBA) (100 g, 0.58 mol) was added portionwise, and the mixture was stirred at room temperature for 18 h. The white precipitate was quenched with saturated aqueous solution of NaHCO$_3$, extracted with DCM (3×250 mL) and washed again with saturated aqueous solution of NaHCO$_3$ (3×250 mL). The organic layers were combined, dried over anhydrous Na$_2$SO$_4$ and concentrated in vacuo. The resulting oil was purified on silica gel (Hexane-EtOAc; 15:1) to provide epoxide as a colourless oil (64.5 g, 82%). To a solution of racemic epoxide (30 g, 0.15 mol) in anhydrous THF (7.5 mL) (R,R)-(−)-N,N'-Bis(3,5-di-tert-butylsalicylidene)-1,2-cyclohexanediaminocobalt(II) [(R,R)Co(II) complex] (448 mg, 0.74 mmol) was added, followed by AcOH (0.14 mL). The solution was cooled to 0° C. and water (1.2 mL) was added dropwise. The reaction was allowed to warm to room temperature and stirred for 18 h. After that time, the volatile materials were concentrated in vacuo and the crude was directly loaded on a silica gel column. Flash chromatography using Hexane/EtOAc (15:1 to 12:1) as eluent, provided chiral epoxide (+)-2 (13.6 g, yield: 46%) as a colourless oil.

$[\alpha]_D$=+14.1 (c 1, CHCl$_3$).

$^1$H NMR (CDCl$_3$, 300 MHz) δ: 3.74 (t, 2H, J=6.3 Hz), 3.01 (m, 1H), 2.74 (t, 1H, J=4.6 Hz), 2.48 (dd, 1H, J=5.1, 3.1 Hz), 1.70 (m, 2H), 0.87 (s, 9H), 0.04 (s, 6H).

$^{13}$C NMR (CDCl$_3$, 75 MHz) δ: 60.2, 50.2, 47.3, 36.1, 26.1, 18.4, −5.2.

Synthesis of Intermediate 3

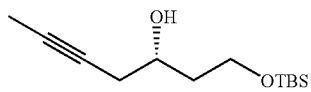 [SMILES: CC#CC[C@H](O)CCO[Si](C)(C)C(C)(C)C]

Propyne (10 mL, 0.176 mol) was condensed at −78° C. and dissolved in anhydrous THF (165 mL). n-Butyllithium (75.1 mL, 0.188 mol) was added dropwise under N$_2$ over 30 min, and the resultant white suspension was stirred for additional 30 min at −78° C. A solution of (+) (R)-2-[2-(tert-butyldimethylsilyloxy)ethyl]oxirane 2 (23.7 g, 0.117 mol)) in anhydrous THF (125 mL) was then added dropwise followed by addition of BF$_3$.OEt$_2$ (22.1 mL, 0.176 mol). The mixture was stirred for 1 h at −78° C. and for an additional hour at 0° C. The reaction mixture was quenched with saturated aqueous solution of NH$_4$Cl (150 mL) and extracted with Et$_2$O (3×150 mL). The combined organic layers were dried over Na$_2$SO$_4$, filtered, and concentrated. Flash chromatography (hexane/EtOAc 10:1 to 1:1) provided alcohol 3 (22.7 g, yield: 80%) as a colourless oil.

$[\alpha]_D$=+5.6 (c 0.1, CHCl$_3$).

$^1$H-NMR (500 MHz, CDCl$_3$) δ: 3.75-3.90 (m, 3H), 3.47 (d, 1H, J=2.7 Hz, OH), 2.34 (m, 2H), 1.79, (t, 3H, J=2.4 Hz), 1.75 (m, 2H), 0.89 (s, 9H), 0.07 (s, 6H).

$^{13}$C-NMR (125 MHz, CDCl$_3$) δ: 77.8, 75.8, 70.7, 62.4, 37.6, 27.6, 26.1, 18.3, 3.7, −5.3, −5.4

MS (ES) m/z 243.2 [M+H]$^+$, 265.2 [M+Na]$^+$..

Synthesis of Intermediate 4

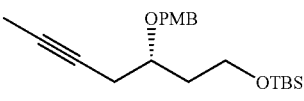

Over a solution of 3 (41.8 g, 0.173 mol) and 18-crown-6 ether (50.27 g, 0.190 mol) in anhydrous THF (1190 mL) at −78° C. under $N_2$ atmosphere, a 0.5N solution of KHMDS in toluene (380 mL, 0.190 mol) was added via addition funnel over a period of 30 min. The mixture was stirred at this temperature for 45 min, followed by addition of a solution of 4-methoxybenzyl chloride (PMBCl) (23.89 g, 0.176 mol) in anhydrous THF (100 mL). After 2 h at −78° C., the mixture was quenched with saturated aqueous solution of $NH_4Cl$ (600 mL). The organic layer was separated and the aqueous phase was extracted exhaustively with EtOAc (3×500 mL). The combined organic layers were washed with saturated aqueous solution of NaCl, dried over anhydrous $Na_2SO_4$, filtered, and concentrated to afford 4 as yellow oil, which was used in the next steps without further purification (61.3 g, yield: 99%).

$^1$H NMR (CDCl$_3$, 300 MHz) δ: 7.25 (d, 2H, J=8.7 Hz), 6.90 (d, 2H, J=8.7 Hz), 4.45 (m, 2H), 3.80 (s, 3H), 3.65 (m, 3H), 2.40 (m, 2H), 1.82 (m, 2H), 1.79 (t, 3H, J=2.4 Hz), 0.92 (s, 9H), 0.05 (s, 6H).

Synthesis of Intermediate 5

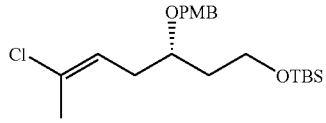

To a solution of 4 (61.3 g, 0.169 mol) in anhydrous toluene (2.1 L), under $N_2$ atmosphere and at 0° C. Schwartz's reagent (Bis(cyclopentadienyl)zirconium(IV) chloride hydride, $Cp_2ZrHCl$) (130.3 g, 0.507 mol) was added and the reaction was stirred 5 min at room temperature. The reaction temperature was increased to 50° C. over a period of 20 min and stirred at 50° C. for 2.5 h. During this time the reaction solution turned of orange colour. The reaction was cooled to 0° C. and N-chlorosuccinimide (58.45 g, 0.440 mol) was added in one portion. Stirring was continued for 30 min at room temperature and the reaction was diluted with Hexane/EtOAc (95:5; 500 mL). Removing of the solid by filtration and evaporation of volatiles provided 5 as yellow oil which was used without further purification (15.1 g, yield: 86%).

$[α]_D$=+20.5 (c 1, CHCl$_3$).

$^1$H NMR (CDCl$_3$, 300 MHz) δ: 7.25 (d, 2H, J=8.7 Hz), 6.87 (d, 2H, J=8.7 Hz), 5.64 (td, 1H, J=7.8, 0.9 Hz), 4.45 (q, 2H, J=11.1 Hz), 3.80 (s, 3H), 3.70 (m, 2H), 3.62 (m, 1H), 2.27 (t, 2H, J=6.9 Hz), 2.03 (s, 3H), 1.70 (m, 2H), 0.89 (s, 9H), 0.05 (s, 6H).

$^{13}$C NMR (CDCl$_3$, 75 MHz) δ: 159.4, 130.9, 130.7, 129.6, 124.2, 114.0, 75.2, 71.4, 59.8, 55.5, 37.7, 33.8, 26.1, 21.2, 18.5, −5.1.

Synthesis of Intermediate 6

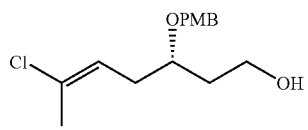

To a solution of 5 (23 g, 0.058 mol) in anhydrous THF (288 ml) under $N_2$ and at 0° C. a solution of Tetrabutylammonium fluoride (TBAF) (115.3 mL, 0.115 mol) was added dropwise over a period of 20 min (the solution turned red). The reaction mixture was stirred at room temperature for 2 h, and then was quenched with saturated aqueous solution of $NH_4Cl$ (200 mL). The layers were separated and the aqueous phase was extracted exhaustively with EtOAc (3×150 mL). The combined organic layers were dried over $Na_2SO_4$, filtered, and concentrated. Flash chromatography (hexane/EtOAc 4:1 to 1:1) provided 6 as a colourless oil (11.9 g, yield: 73%).

$^1$H NMR (CDCl$_3$, 300 MHz) δ: 7.25 (d, 2H, J=8.7 Hz), 6.86 (d, 2H, J=8.7 Hz), 5.62 (t, 1H, J=7.8 Hz), 4.45 (m, 2H), 3.80 (s, 3H), 3.70 (m, 3H), 2.35 (m, 2H), 2.03 (s, 3H), 1.75 (m, 2H).

Synthesis of Intermediate 7

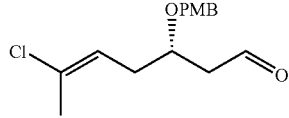

(Diacetoxyiodo)benzene (BAIB) (11.5 g, 35.7 mmol) was added to a solution of alcohol 6 (9.2 g, 32.4 mmol) and 2,2,6,6-Tetramethylpiperidine 1-oxyl (TEMPO) (515 mg, 3.3 mmol) in anhydrous dichloromethane (92 mL). The reaction mixture was stirred at room temperature for 20 h until the alcohol was no longer detectable (TLC), and then it was quenched with a saturated aqueous solution of $NH_4Cl$ and extracted with DCM (3×100 mL). The combined organic phases were dried over anhydrous $Na_2SO_4$, filtered and concentrated. The residue was purified by flash chromatography (Hexane/EtOAc 4:1 to 1:1) to afford 7 as colourless oil (6.3 g, yield: 69%).

$^1$H NMR (CDCl$_3$, 300 MHz) δ: 9.78 (s, 1H), 7.25 (d, 2H, J=8.7 Hz), 6.85 (d, 2H, J=8.7 Hz), 5.64 (t, 1H, J=7.8 Hz), 4.45 (q, 2H, J=11.1 Hz), 4.02 (m, 1H), 3.80 (s, 3H), 2.60 (m, 2H), 2.35 (m, 2H), 2.03 (s, 3H).

$^{13}$C NMR (CDCl$_3$, 75 MHz) δ: 201, 159.6, 132.1, 130.1, 129.7, 122.8, 114.1, 73.3, 71.5, 55.5, 48.3, 33.5, 21.3.

Synthesis of Intermediate 8

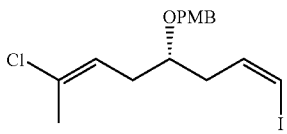

To a suspension of iodomethyltriphenylphosphonium iodide (16.6 g, 31 mmol) in anhydrous THF (126 mL), at room temperature, a 1M solution of NaHMDS in anhydrous THF (31.27 Ml, 31.27 mol) was slowly added. After stirring for 2 min, the yellow mixture was cooled to −78° C. and a solution of 7 (6.3 g, 22 mmol) in anhydrous THF (82 mL) was then added. The reaction mixture was stirred at −78° C. for 2 h, and at room temperature for 5 min, diluted with hexane and filtered through a plug of Celite®. The plug was rinsed with hexane, the combined filtrates were evaporated under reduced pressure and the resulting oil was purified by column chromatography (Hexane/EtOAc 12:1 to 8:1) affording 8 as a yellow oil (5.6 g, yield: 62%).

$^1$H NMR (CDCl$_3$, 300 MHz) δ: 7.25 (d, 2H, J=8.7 Hz), 6.85 (d, 2H, J=8.7 Hz), 6.25 (m, 2H) 5.64 (t, 1H, J=7.8 Hz), 4.42 (m, 2H), 3.80 (s, 3H), 3.55 (m, 1H), 2.40 (m, 2H), 2.25 (m, 2H), 2.03 (s, 3H).

Synthesis of Intermediate 9

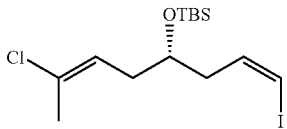 [SMILES: C/C(Cl)=C\C[C@@H](C/C=C\I)O[Si](C)(C)C(C)(C)C]

2,3-Dichloro-5,6-dicyano-p-benzoquinone (DDQ) (3.6 g, 16 mmol) was added to a solution of 8 (5 g, 12 mmol) in DCM-H$_2$O (20:1, 98 mL) under N$_2$ atmosphere at room temperature. After 1.5 h (TLC Hexane/EtOAc 4:1 showed no starting material) the reaction was quenched by pouring into Et$_2$O (200 mL) and washing with 1M NaOH (3×50 mL) and brine (50 mL). The organic phase was dried over anhydrous Na$_2$SO$_4$, filtered and concentrated. Chromatographic separation of p-methoxybenzaldehyde was facilitated by reduction to p-methoxybenzyl alcohol. Towards this end, a solution of the obtained residue in MeOH (98 mL) with NaBH$_4$ (0.60 g, 16 mmol) under N$_2$ atmosphere was maintained at room temperature for 1 h. The reaction mixture was then quenched by pouring into Et$_2$O (100 mL) and washing with 1M HCl (40 mL) and brine (40 mL). The organic phase was dried over anhydrous Na$_2$SO$_4$, filtered and concentrated. The resulting oil was purified on silica gel (Hexane/EtOAc 10:1 to 4:1) to provide the secondary alcohol as colourless oil (2.8 g, yield: 80%).

To a solution of secondary alcohol (2.8 g, 10 mmol) in anhydrous DCM (38 mL) under N$_2$ atmosphere and at 0° C., 2,6-lutidine (2.28 mL, 20 mmol) was added dropwise, followed by addition of tert-Butyldimethylsilyl trifluoromethanesulfonate (TBSOTf) (2.33 mL, 12 mmol). The reaction mixture was stirred for 2 h. At this point the crude was quenched with 0.5M HCl (25 mL) and extracted with DCM (2×25 mL). The combined organic layers were washed with a saturated aqueous solution of NaHCO$_3$ and brine. The organic phase was dried over Na$_2$SO$_4$, filtered, and concentrated. Flash chromatography (Hexane/EtOAc 100:1 to 20:1) provided 9 as a colourless oil (3.14 g, yield: 80%).

$^1$H NMR (CDCl$_3$, 300 MHz) δ: 6.25 (m, 2H) 5.64 (t, 1H, J=7.8 Hz), 3.82 (m, 1H), 2.38 (t, 2H, J=6.0 Hz), 2.20 (t, 2H, J=6.3 Hz), 2.03 (s, 3H), 0.86 (s, 9H), 0.05 (s, 6H).

$^{13}$C NMR (CDCl3, 75 MHz) δ: 137.7, 130.9, 124.3, 84.6, 70.6, 42.5, 36.6, 25.9, 21.3, 18.2, −4.4.

Synthesis of Intermediate 10a

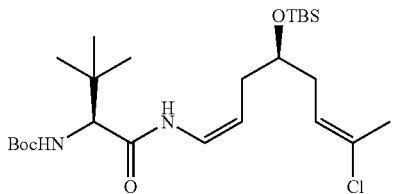 [SMILES: C/C(Cl)=C\C[C@@H](C/C=C\NC(=O)[C@@H](NC(=O)OC(C)(C)C)C(C)(C)C)O[Si](C)(C)C(C)(C)C]

A resealable Schlenk tube was charged with copper (I) iodide (148 mg, 0.78 mmol), potassium carbonate (1.076 g, 7.78 mmol) and Boc-tert-LeuCONH$_2$ (prepared following the procedure described in Pozdnev, V. F., *Tetrahedron Letters* 1995, 36, 7115-7118) (0.96 g, 4.15 mmol), evacuated and filled with N$_2$. N,N'-Dimethylethylenediamine (DMEDA) (0.166 mL, 1.55 mmol), vinyl iodide 9 (1.04 g, 2.59 mmol) and anhydrous DMF (15 mL) were added under N$_2$. The Schlenk tube was sealed, heated at 90° C. for 18 h and cooled to room temperature. The resultant mixture was diluted with EtOAc and quenched with water. The organic layer was washed with water and dried over anhydrous Na$_2$SO$_4$. The solvent was removed under reduced pressure and the residue was purified by flash chromatography on silica gel (Hexane/EtOAc, 20:1 to 15:1). Intermediate 10a (670 mg, yield: 53%) was obtained as an oil.

$^1$H NMR (CDCl$_3$, 300 MHz) δ: 7.72 (d, 1H, J=9.9 Hz), 6.70 (t, 1H, J=9.6 Hz), 5.54 (t, 1H, J=7.8 Hz), 5.35 (d, 1H, J=9.0 Hz), 4.76 (q, 1H, J=7.8 Hz), 3.89 (d, 1H, J=9.0 Hz), 3.73-3.68 (m, 1H), 2.12 (m, 4H), 1.98 (s, 3H), 1.40 (s, 9H), 0.97 (s, 9H), 0.84 (s, 9H), 0.02 (s, 3H), 0.01 (s, 3H).

$^{13}$C NMR (CDCl$_3$, 75 MHz) δ: 168.9, 156.0 131.1, 123.9, 122.6, 108.2, 79.9, 71.6, 62.5, 36.5, 34.8, 33.8, 28.1, 26.7, 25.9, 21.2, 18.3, −4.3, −4.4.

Synthesis of Intermediate 10b

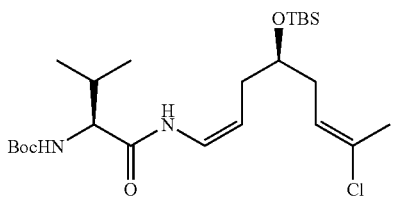 [SMILES: C/C(Cl)=C\C[C@@H](C/C=C\NC(=O)[C@@H](NC(=O)OC(C)(C)C)C(C)C)O[Si](C)(C)C(C)(C)C]

A resealable Schlenk tube was charged with copper (I) iodide (40.4 mg, 0.213 mmol), potassium carbonate (294 mg, 2.13 mmol) and Boc-Val-CONH$_2$ (prepared following the procedure described in Pozdnev, V. F., *Tetrahedron Letters* 1995, 36, 7115-7118) (230 mg, 1.06 mmol), evacuated and filled with N$_2$. N,N'-Dimethylethylenediamine (45 µL, 0.426 mmol), vinyl iodide 9 (283 mg, 0.71 mmol) and anhydrous DMF (35 mL) were added under N$_2$. The Schlenk tube was sealed, heated at 90° C. for 16-18 h and cooled to room temperature. The resultant mixture was diluted with EtOAc and quenched with water. The organic layer was washed with water and dried over anhydrous $Na_2SO_4$. The solvent was removed under reduced pressure and the residue was purified by flash chromatography on silica gel (Hexane/EtOAc, 7:1 to 3:1). Intermediate 10b (270 g, yield: 77%) was obtained as an oil.

$^1$H NMR (CDCl$_3$, 300 MHz) δ: 7.80 (d, 1H, J=9.3 Hz), 6.79-6.73 (m, 1H), 5.58 (t, 1H, J=7.5 Hz), 5.02 (br s, 1H), 4.85-4.76 (m, 1H), 3.93 (dd, 1H, J=8.4, 6.0 Hz), 3.80-3.73 (m, 1H), 2.12-2.22 (m, 5H), 2.02 (s, 3H), 1.45 (s, 9H), 0.98 (d, 3H, J=6.9 Hz), 0.93 (d, 3H, J=6.9 Hz), 0.89 (s, 9H), 0.07 (s, 3H), 0.06 (s, 3H).

Synthesis of Intermediate 11a

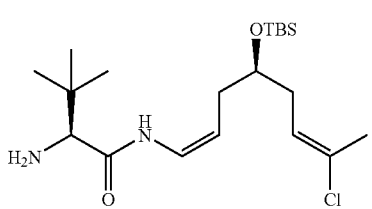 [SMILES: C/C(Cl)=C\C[C@@H](C/C=C\NC(=O)[C@@H](N)C(C)(C)C)O[Si](C)(C)C(C)(C)C]

A solution of amino protected derivative 10a (670 mg, 1.33 mmol) in ethylenglycol (30 mL) was heated at 200° C. for 15 min. The reaction mixture was then cooled at room temperature, diluted with DCM, quenched with brine and poured into water. A few drops of 3M NaOH were added until the solution reached pH 14 and then was extracted thoroughly with DCM. The combined organic phases were dried over anhydrous $Na_2SO_4$, filtrated and concentrated in vacuo to afford the primary amine 11a (510 mg, yield: 95%) as a yellow oil which was used without further purification.

$^1$H NMR (CDCl$_3$, 300 MHz) δ: 8.77 (d, 1H, J=9.9 Hz), 6.71 (t, 1H, J=9.6 Hz), 5.56 (t, 1H, J=7.8 Hz), 4.71 (m, 1H), 3.72 (m, 1H), 3.14 (s, 1H), 2.14 (m, 4H), 1.97 (s, 3H), 0.97 (s, 9H), 0.84 (s, 9H), 0.02 (s, 6H).

$^{13}$C NMR (CDCl$_3$, 75 MHz) δ: 171.2, 131.0, 124.1, 122.5, 107.1, 71.5, 64.3, 36.2, 34.5, 33.8, 26.5, 26.0, 21.2, 18.2, −4.4, −4.5.

Synthesis of Intermediate 11b

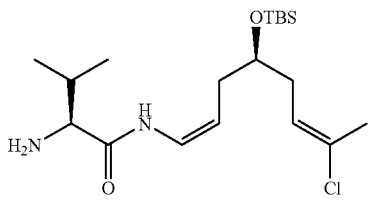 [SMILES: C/C(Cl)=C\C[C@@H](C/C=C\NC(=O)[C@@H](N)C(C)C)O[Si](C)(C)C(C)(C)C]

A solution of amino protected derivative 10b (255 mg, 0.52 mmol) in ethylenglycol (15 mL) was heated at 200° C. for 15 min. The reaction mixture was then cooled at room temperature, diluted with DCM, quenched with brine and poured into water. A few drops of 3M NaOH were added until the solution reached pH 14 and then was extracted thoroughly with DCM. The combined organic phases were dried over anhydrous $Na_2SO_4$, filtrated and concentrated in vacuo to afford the primary amine 11b (170 mg, yield: 85%) as a yellow oil which was used without further purification.

$^1$H NMR (CDCl$_3$, 300 MHz) δ: 9.27 (d, 1H, J=10.2 Hz), 6.76 (dd, 1H, J=11.1, 9.6 Hz), 5.61 (t, 1H, J=7.8 Hz), 4.80-4.72 (m, 1H), 3.81-3.73 (m, 1H), 3.31 (d, 1H, J=3.6 Hz) 2.44-2.33 (m, 1H), 2.20-2.16 (m, 4H), 2.03 (s, 3H), 1.59 (br s, 2H), 1.00 (d, 3H, J=6.9 Hz), 0.89 (s, 9H), 0.82 (d, 3H, J=6.9 Hz), 0.05 (s, 6H).

$^{13}$C NMR (CDCl$_3$, 75 MHz) δ: 172.1, 131.1, 124.1, 122.5, 107.4, 71.5, 60.2, 36.2, 33.7, 30.8, 26.0, 21.3, 20.0, 18.3, 16.1, −4.3, −4.4.

Synthesis of Intermediate 12a

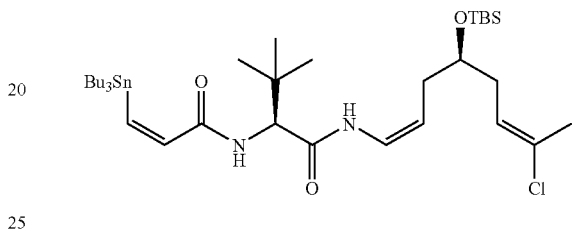

To a solution of amine 11a (918 mg, 2.27 mmol) in anhydrous DCM/DMF (10:1, 39.6 mL), a solution of (Z)-3-tributylstannylpropenoic acid (1028 mg, 2.84 mmol) in anhydrous DCM was added, under $N_2$ atmosphere, and then was cooled at 0° C. Diisopropylethylamine (DIPEA) (0.6 mL, 3.4 mmol), 1-Hydroxy-7-azabenzotriazole (HOAt) (310 mg, 2.27 mmol), and N,N,N',N'-Tetramethyl-O-(7-azabenzotriazol-1-yl)uronium hexafluorophosphate (HATU) (860 mg, 2.27 mmol) were added to the solution and after 30 min the cold bath was removed. The reaction mixture was stirred at room temperature for 2 h, quenched with a saturated aqueous solution of NH$_4$Cl, poured into water and extracted with DCM. The combined organic phases were dried over anhydrous $Na_2SO_4$, filtered and concentrated. The residue was purified by flash chromatography (Hexane/EtOAc 20:1 to 15:1) to give amide 12a (1.11 g; yield: 66%) as an oil.

$^1$H NMR (CDCl$_3$, 300 MHz) δ: 7.63 (d, 1H, J=10.5 Hz), 6.97 (d, 1H, J=12.3 Hz), 6.75 (d, 1H, J=12.3 Hz), 6.72 (t, 1H, J=9.5 Hz), 6.50 (d, 1H, J=9.0 Hz), 5.56 (t, 1H, J=6.6 Hz), 4.83 (q, 1H, J=9.0 Hz), 4.41 (d, 1H, J=9.6 Hz) 3.76 (m, 1H), 2.17 (m, 4H), 2.01 (s, 3H), 1.45 (m, 6H), 1.25 (m, 8H), 1.0 (s, 9H), 0.88 (s, 9H), 0.84 (m, 13H), 0.06 (s, 6H).

Synthesis of Intermediate 12b

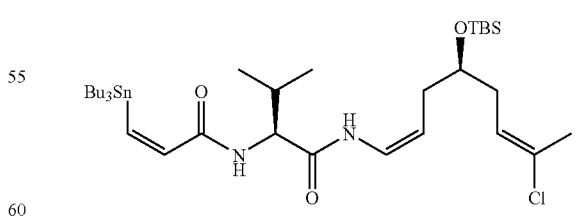

To a solution of amine 11b (170 mg, 0.437 mmol) in anhydrous DCM/DMF (10:1, 7.7 mL), a solution of (Z)-3-tributylstannylpropenoic acid (197.2 mg, 0.546 mmol) in anhydrous DCM was added, under $N_2$ atmosphere, and then was cooled at 0° C. DIPEA (0.11 mL, 0.655 mmol), HOAt (59.4 mg, 0.437 mmol), and HATU (166 mg, 0.437 mmol)

were added to the solution and after 30 min the cold bath was removed. The reaction mixture was stirred at room temperature for 2 h, quenched with a saturated aqueous solution of NH$_4$Cl, poured into water and extracted with DCM. The combined organic phases were dried over anhydrous Na$_2$SO$_4$, filtered, and concentrated. The residue was purified by flash chromatography (Hexane/EtOAc 20:1 to 15:1) to give amide 12b (250 mg, yield: 78%) as a white foam.

$^1$H NMR (CDCl$_3$, 300 MHz) δ: 7.94 (d, 1H, J=10.8 Hz), 7.00 (d, 1H, J=12.3 Hz), 6.75 (d, 1H, J=12.3 Hz), 6.72 (t, 1H, J=9.5 Hz), 6.50 (d, 1H, J=9.0 Hz), 5.56 (t, J=6.6 Hz, 1H), 4.83 (q, 1H, J=9.0 Hz), 4.41 (t, 1H, J=9.0 Hz), 3.76 (m, 1H), 2.17 (m, 4H), 2.01 (s, 3H), 1.45 (m, 7H), 1.25 (m, 8H), 0.88 (s, 9H), 0.84 (m, 19H), 0.06 (s, 6H).

$^{13}$C NMR (CDCl$_3$, 75 MHz) δ: 169.2, 166.8, 153.8, 136.2, 131.1, 123.9, 122.6, 108.7, 71.6, 59.2, 36.5, 33.7, 31.4, 29.5, 27.6, 26.1, 21.3, 19.5, 18.5, 14.0, 11.8, −4.3, −4.4.

Synthesis of Intermediate 13a

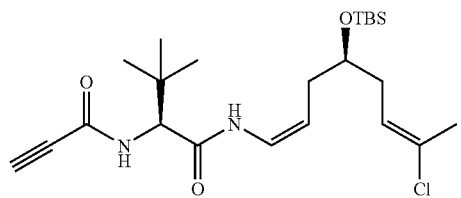 [SMILES: C#CC(=O)N[C@H](C(=O)N/C=C\C[C@H](C/C=C(\C)Cl)O[Si](C)(C)C(C)(C)C)C(C)(C)C]

To a solution of 11a (120 mg, 0.30 mmol) and propiolic acid (23 μL, 0.37 mmol) in anhydrous DCM/DMF 10:1 (4.2 mL) at 0° C., HATU (113 mg, 0.30 mmol), HOAt (40 mg, 0.30 mmol) and DIPEA (0.78 μL, 0.44 mmol) were added. The reaction was stirred at 0° C. for 30 min and 2 hours at room temperature. Then, the crude mixture was treated with a saturated aqueous solution of NH$_4$Cl and extracted with CH$_2$Cl$_2$. The combined filtrates were washed with H$_2$O. After drying and evaporating the solvent under reduced pressure the crude was purified by column chromatography (Ethyl acetate/hexanes mixture) to afford pure compound 13a (50 mg, yield: 40%).

$^1$H NMR (CDCl$_3$, 300 MHz) δ: 8.20 (d, 1H, J=10.2 Hz), 6.83 (d, 1H, J=9.6 Hz), 6.72 (t, 1H, J=9.3 Hz), 5.55 (t, 1H, J=6.9 Hz), 4.88 (q, 1H, J=8.7 Hz), 4.58 (d, 1H, J=9.6 Hz), 3.75 (m, 1H), 2.90 (s, 1H), 2.17 (m, 4H), 2.00 (s, 3H), 1.02 (s, 9H), 0.87 (s, 9H), 0.05 (s, 3H), 0.04 (s, 3H).

$^{13}$C NMR (CDCl$_3$, 75 MHz) δ: 167.5, 152.1, 131.0, 124.1, 122.3, 109.4, 77.1, 74.8, 71.7, 60.9, 36.5, 35.7, 33.8, 26.7, 26.1, 21.2, 18.3, −4.3, −4.4.

Synthesis of Intermediate 13b

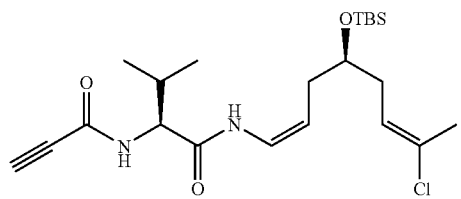 [SMILES: C#CC(=O)N[C@H](C(=O)N/C=C\C[C@H](C/C=C(\C)Cl)O[Si](C)(C)C(C)(C)C)C(C)C]

To a solution of 11b (200 mg, 0.51 mmol) and propiolic acid (39 μL, 0.64 mmol) in anhydrous DCM/DMF 10:1 (8 mL) at 0° C., HATU (194 mg, 0.51 mmol), HOAt (69 mg, 0.51 mmol) and DIPEA (133 μL, 0.76 mmol) were added. The reaction was stirred at 0° C. for 30 min and 2 hours at room temperature. Then, the crude mixture was treated with a saturated aqueous solution of NH$_4$Cl and extracted with CH$_2$Cl$_2$. The combined filtrates were washed with H$_2$O. After drying and evaporating the solvent under reduced pressure the crude was purified by column chromatography (Ethyl acetate/hexanes mixture) to afford pure compound 13b (150 mg, yield: 67%).

$^1$H NMR (CDCl$_3$, 300 MHz) δ: 7.02 (d, 1H, J=11.4 Hz), 6.75 (dd, 1H, J=10.8, 9.0 Hz), 6.53 (d, 1H, J=10.2 Hz), 5.58 (dd, 1H, J=9.0, 7.8 Hz), 4.87 (q, 1H, J=7.8 Hz), 4.33 (dd, 1H, J=8.7, 6.3 Hz), 3.84-3.76 (m, 1H), 2.83 (s, 1H), 2.23-2.11 (m, 5H), 2.05-2.03 (m, 3H), 0.99 (d, 6H, J=6.9 Hz), 0.89 (s, 9H), 0.08 (s, 3H), 0.06 (s, 3H).

Example 2

Synthesis of Fragment 18

Scheme 2 provides an example of the synthesis of fragment 18.

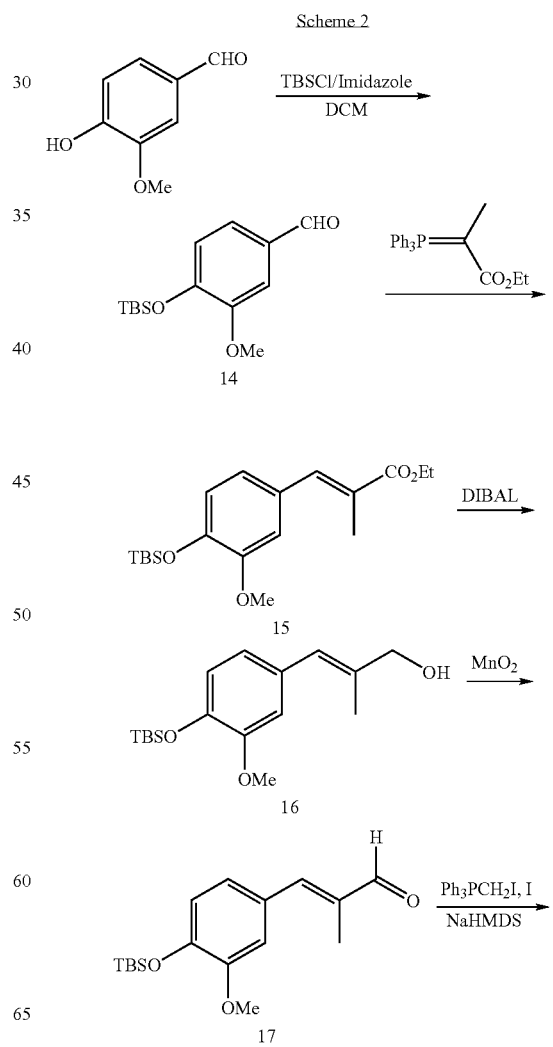

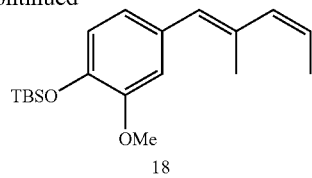

18

Synthesis of Intermediate 14

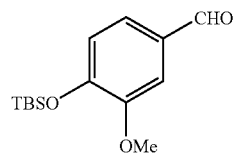 [SMILES: COc1cc(C=O)ccc1O[Si](C)(C)C(C)(C)C]

To a solution of 4-hydroxy-3-methoxybenzaldehyde (1 g, 6.57 mmol) in anhydrous DCM (14 mL), under N$_2$ atmosphere and at 0° C., imidazole (1.118 g, 8.21 mmol) and tert-Butyldimethylsilylchloride (1.084 g, 7.22 mmol) were added. After 3 hours at room temperature the reaction was quenched with a solution of HCl 0.5N and diluted with CH$_2$Cl$_2$ (100 mL). The combined organic layers were washed with a saturated aqueous solution of NaHCO$_3$ and brine. The organic phase was dried over anhydrous Na$_2$SO$_4$, filtered, and concentrated to afford 1.71 g (yield: 98%) of aldehyde 14.

$^1$H NMR (CDCl$_3$, 300 MHz) δ: 9.84 (s, 1H), 7.40-7.36 (m, 2H), 6.96 (d, 1H, J=7.8 Hz), 3.87 (s, 3H), 1.00 (s, 9H), 0.19 (s, 6H).

Synthesis of Intermediate 15

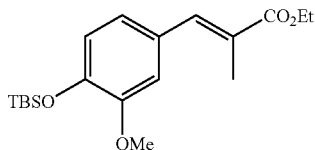 [SMILES: CCOC(=O)/C(C)=C/c1ccc(O[Si](C)(C)C(C)(C)C)c(OC)c1]

Over a solution of aldehyde 14 (1 g, 3.75 mmol) in toluene (20 mL) Carboethoxyethylidene-triphenylphosphorane (3.4 g, 9.38 mmol) was added and the mixture was heated at 60° C. over 2.5 h. Then, the solvent was removed under reduced pressure and the resulting oil was purified by column chromatography (hexane/EtOAc 12:1) affording 1.1 g (yield: 81%) of ester compound 15.

$^1$H NMR (CDCl$_3$, 300 MHz) δ: 7.62 (s, 1H), 6.96-6.85 (m, 3H), 4.26 (q, 2H, J=7.2 Hz), 3.82 (s, 3H), 2.14 (s, 3H), 1.34 (t, 3H, J=7.2 Hz), 1.00 (s, 9H), 0.18 (s, 6H).

Synthesis of Intermediate 16

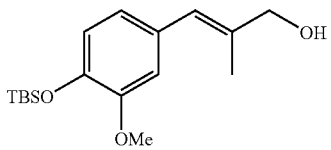 [SMILES: COc1cc(/C=C(\C)CO)ccc1O[Si](C)(C)C(C)(C)C]

Over a −78° C. cooled solution of ester 15 (640 mg, 1.746 mmol) in anhydrous THF (8.7 mL) under N$_2$ atmosphere, Diisobutylaluminum hydride (DIBAL) 1M in toluene (3.84 mL, 3.84 mmol) was added over a period of 10 min and the mixture was stirred at −78° C. After 4 hours the reaction was quenched with MeOH (0.16 mL) and a saturated aqueous solution of sodium potassium tartrate was added (15 mL) and diluted with EtOAc. This mixture was stirred for 1 h and then the organic layer was decanted. The aqueous residue was extracted with additional EtOAc and the combined organic layers were dried over anhydrous Na$_2$SO$_4$ and the solvent was evaporated. The resulting oil was purified by column chromatography (hexane/EtOAc 9:1 to 6:4) affording 360 mg (yield: 68%) of alcohol 16.

$^1$H NMR (CDCl$_3$, 300 MHz) δ: 6.80-6.76 (m, 3H), 6.43 (br s, 1H), 4.16 (d, 2H, J=3.3 Hz), 3.79 (s, 3H), 1.91 (s, 3H), 1.00 (s, 9H), 0.16 (s, 6H).

Synthesis of Intermediate 17

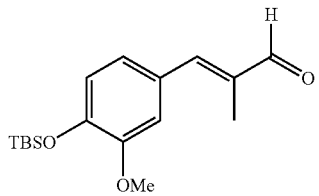 [SMILES: COc1cc(/C=C(\C)C=O)ccc1O[Si](C)(C)C(C)(C)C]

Over a solution of alcohol 16 (270 mg, 0.875 mmol) in ethyl ether (4.4 mL) under N$_2$ atmosphere, MnO$_2$ (1.141 g, 13.12 mmol) was added and the mixture was stirred at room temperature for 2 hours. This mixture was filtrated over a silica gel column eluting with EtOAc and the resulting solution was dried under reduced pressure to afford 256 mg (yield: 96%) of aldehyde 17.

$^1$HNMR (CDCl$_3$, 300 MHz) δ: 9.54 (s, 1H), 7.18 (br s, 1H), 7.109-7.081 (m, 2H), 6.92 (d, 1H, J=8.1 Hz), 3.86 (s, 3H), 2.10 (s, 3H), 1.00 (s, 9H), 0.19 (s, 6H).

Synthesis of Intermediate 18

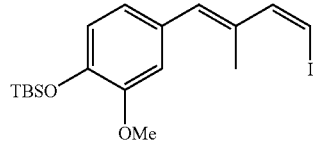 [SMILES: COc1cc(/C=C(C)/C=C\I)ccc1O[Si](C)(C)C(C)(C)C]

To a suspension of iodomethyl triphenylphosphonium iodide (Gilbert Stork, K Z. *Tetrahedron letters* 1989, 30 (17), 2173) (605 mg, 1.142 mmol) in THF (4.6 mL) at room temperature, a 1M solution of sodium hexamethyldisilazane (NaHMDS) (1.142 mL, 1.142 mmol) was slowly added. After stirring for an additional 2 min, the solution was cooled to −78° C. and a solution of aldehyde 17 (250 mg, 0.815 mmol) in THF (3 mL) was added. The temperature was kept at −78° C. while the reaction mixture was stirred for 2 hours. Hexane was added and the resulting slurry was filtrated over Celite® and washed with additional hexane. The filtrate was evaporated under reduced pressure and the resulting oil was purified by column chromatography (hexane/EtOAc 100:0 to 20:1) affording 250 mg (yield: 71%) of iodide 18.

$^1$HNMR (CDCl$_3$, 300 MHz) δ: 6.92 (d, 1H, J=8.1 Hz), 6.83 (br s, 3H), 6.66 (s, 1H), 6.25 (d, 1H, J=8.1 Hz) 3.82 (s, 3H), 2.18 (s, 3H), 1.00 (s, 9H), 0.18 (s, 6H).

Example 3

Synthesis of Fragment 22

Scheme 3 provides an example of the synthesis of fragment 22.

Scheme 3

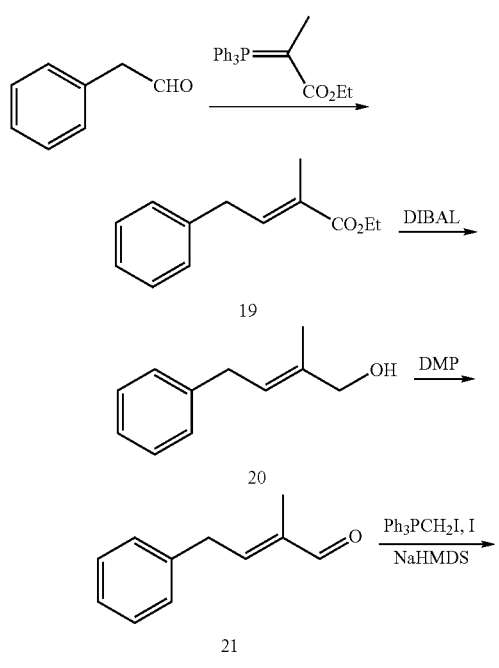

Synthesis of Intermediate 19

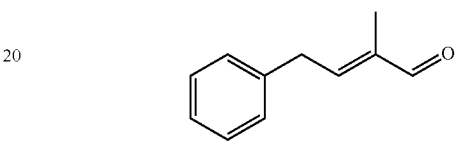

Over a solution of Phenylacetaldehyde (100 mg, 0.83 mmol) in toluene (5.0 mL) Carboethoxyethylidene-triphenylphosphorane (754 mg, 2.08 mmol) was added and the mixture was stirred at room temperature over 18 h. Then, the solvent was removed under reduced pressure and the resulting oil was purified by column chromatography (Ethyl acetate/hexanes mixture) affording pure 150 mg (90% yield) of ester compound 19.

$^1$H NMR (CDCl$_3$, 300 MHz) δ: 7.35-7.18 (m, 5H), 6.94 (t, 1H, J=7.5 Hz), 4.20 (q, 2H, J=7.2 Hz), 3.54 (d, 2H, J=7.8 Hz), 1.97 (s, 3H), 1.29 (t, 3H, J=7.2 Hz).

Synthesis of Intermediate 20

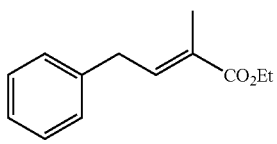

Over a −78° C. cooled solution of ester 19 (150 mg, 0.73 mmol) in anhydrous THF (3.6 mL) under N$_2$ atmosphere, Diisobutylaluminum hydride (DIBAL) 1M in toluene (1.62 mL, 1.62 mol) was added over a period of 5 min and the mixture was stirred at −78° C. After 4 hours the reaction was quenched with MeOH (0.7 mL) and a saturated aqueous solution of sodium potassium tartrate was added (4 mL) and diluted with EtOAc (10 mL). This mixture was stirred for 2 h and then the organic layer was decanted. The aqueous residue was extracted with additional EtOAc (2×15 mL) and the combined organic layers were dried (anhydrous Na$_2$SO$_4$) and the solvent was evaporated affording 110 mg (yield: 92%) of alcohol 20, which was used without further purification.

$^1$H NMR (CDCl$_3$, 300 MHz) δ: 7.32 (m, 3H), 7.23 (m, 2H), 5.64 (t, 1H, J=6.3 Hz), 4.04 (s, 2H), 3.43 (d, 2H, J=7.2 Hz), 2.19 (bs, 1H), 1.80 (s, 3H).

Synthesis of Intermediate 21

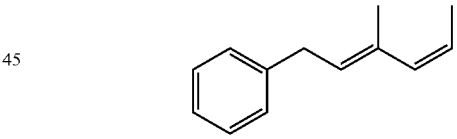

Over a solution of alcohol 20 (96 mg, 0.59 mmol) in Dichloromethane (3.8 mL) under N$_2$ atmosphere, Dess Martin periodinane (DMP) (502 mg, 1.18 mol) was added and the mixture was stirred at room temperature for 2 hours. This mixture was quenched with a saturated aqueous solution of NH$_4$Cl (3 mL) and diluted with Dichloromethane (5 mL). The organic phase was dried over anhydrous Na$_2$SO$_4$, and evaporated at reduced pressure. Purification by column chromatography (hexane/Ethyl acetate 10:1) afforded pure aldehyde 21 (75 mg, yield: 80%)

$^1$H NMR (CDCl$_3$, 300 MHz) δ: 9.43 (s, 1H), 7.35-7.18 (m, 5H), 6.64 (t, 1H, J=7.2 Hz), 3.43 (d, 2H, J=7.2 Hz), 1.88 (s, 3H).
$^{13}$C NMR (CDCl$_3$, 75 MHz) δ: 195.3, 152.4, 139.8, 138.4, 129.1, 128.7, 127.0, 62.2, 35.4.

Synthesis of Intermediate 22

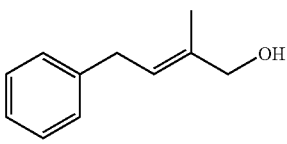

To a suspension of iodomethyl triphenylphosphonium iodide (Gilbert Stork, K Z. *Tetrahedron letters* 1989, 30(17), 2173) (347 mg, 0.66 mmol) in THF (2.7 mL) at room temperature, a 1M solution in THF of sodium hexamethyldisilazane (NaHMDS) (0.66 mL, 0.66 mmol) was slowly added. After stirring for an additional 2 min, the solution was cooled to −78° C. and a solution of aldehyde 21 (75 mg, 0.47 mmol) dissolved in THF (1.75 mL) was added.

The temperature was kept at −78° C. while the reaction mixture was stirred for 2 hours. Hexane (25 mL) was added and the resulting slurry was filtrated over Celite® and washed with additional hexane (50 mL). The filtrate was evaporated under reduced pressure and the resulting oil was purified by column chromatography (hexane/EtOAc 20:1 to 15:1) affording 82 mg (yield: 62%) of iodide 22.

$^1$H NMR (CDCl$_3$, 300 MHz) δ: 7.35-7.18 (m, 5H), 6.82 (d, 1H, J=8.4 Hz), 6.17 (dd, 1H, J=8.4 Hz), 5.90 (tt, 1H, J=7.5, 1.2 Hz), 3.50 (d, 2H, J=7.5 Hz), 2.03 (s, 3H).

Example 4

Synthesis of Fragment 26

Scheme 4 provides an example of the synthesis of fragment 26.

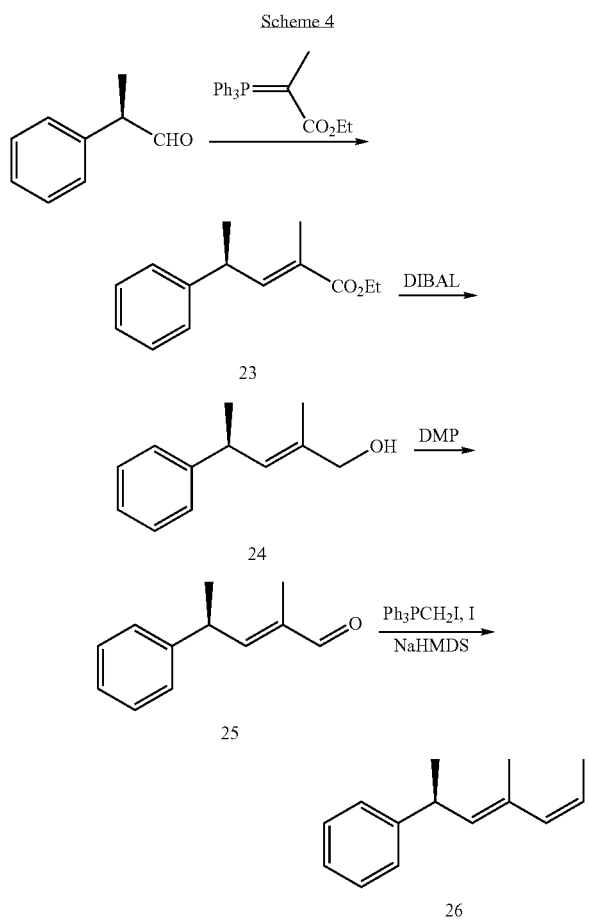

Scheme 4

Synthesis of Intermediate 23

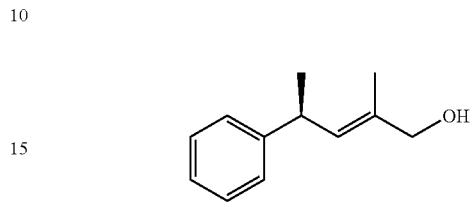

Over a solution of (R)-2-Phenylpropanal (prepared following the procedure described in *Tetrahedron Asymmetry* 1998, 1929-1931) (80 mg, 0.59 mmol) in toluene (2.8 mL) Carboethoxyethylidene-triphenylphosphorane (540 mg, 1.49 mmol) was added and the mixture was stirred at room temperature over 4 h. Then, the solvent was removed under reduced pressure and the resulting oil was purified by column chromatography (hexane/EtOAc 10:1) affording 70 mg (55 yield) of ester compound 23.

$^1$H NMR (CDCl$_3$, 300 MHz) δ: 7.34-7.19 (m, 5H), 6.87 (dq, 1H, J=9.9, 1.4 Hz), 4.18 (q, 2H, J=7.1 Hz), 3.80 (m, 1H), 1.92 (d, 3H, J=1.4 Hz), 1.41 (d, 3H, J=7.0 Hz), 1.29 (t, 3H, J=7.1 Hz).

Synthesis of Intermediate 24

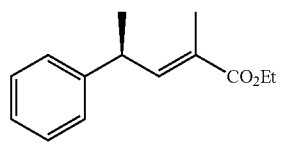 [SMILES: CCOC(=O)/C(C)=C/[C@H](C)c1ccccc1]

Over a −78° C. cooled solution of ester 23 (70 mg, 0.321 mmol) in anhydrous THF (1.6 mL) under N$_2$ atmosphere, diisobutylaluminum hydride (DIBAL) 1M in toluene (0.71 mL, 0.71 mmol) was added and the mixture was stirred at −78° C. After 4 hours the reaction was quenched with MeOH (0.4 mL) and a saturated aqueous solution of sodium potassium tartrate was added (1.5 mL) and diluted with EtOAc (6 mL). This mixture was stirred for 1 h and then the organic layer was decanted. The aqueous residue was extracted with additional EtOAc (2×6 mL) and the combined organic layers were dried (anhydrous Na$_2$SO$_4$) and the solvent was evaporated. The resulting oil was purified by column chromatography (hexane/EtOAc 6:1) affording 40 mg (75% yield) of alcohol 24 as a colourless oil.

$^1$H NMR (CDCl$_3$, 300 MHz) δ: 7.34-7.16 (m, 5H), 5.57 (dq, 1H, J=9.4, 1.2 Hz), 4.00 (s, 2H), 3.71 (m, 1H), 1.75 (d, 3H, J=1.2 Hz), 1.35 (d, 3H, J=7.0 Hz).

$^{13}$C NMR (CDCl$_3$, 75 MHz) δ: 146.7, 133.9, 131.4, 128.7, 127.1, 126.2, 68.9, 37.9, 22.3, 14.1.

Synthesis of Intermediate 25

Over a solution of alcohol 24 (40 mg, 0.226 mmol) in dichloromethane (1.5 mL) under N$_2$ atmosphere, Dess Martin periodinane (DMP) (193 mg, 0.454 mol) was added and the mixture was stirred at room temperature for 2 hours. This mixture was quenched with a saturated aqueous solution of NaHCO$_3$ (2 mL) and diluted with dichloromethane (5 mL). The organic phase was dried over anhydrous Na$_2$SO$_4$ and evaporated under reduced pressure. Purification by column chromatography (hexane/EtOAc 10:1) afforded pure aldehyde 25 (18 mg, 50% yield) as a colourless oil.

$^1$H NMR (CDCl$_3$, 300 MHz) δ: 9.42 (s, 1H), 7.39-7.23 (m, 5H), 6.56 (dq, 1H, J=9.7, 0.9 Hz), 4.00 (m, 1H), 1.83 (s, 3H), 1.47 (d, 3H, J=7.0 Hz).

$^{13}$C NMR (CDCl$_3$, 75 MHz) δ: 195.6, 158.2, 143.8, 137.9, 129.1, 127.2, 127.1, 39.1, 21.1, 9.6.

Synthesis of Intermediate 26

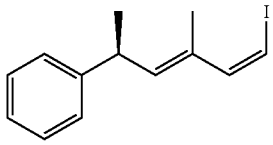

To a suspension of iodomethyl triphenylphosphonium iodide (Gilbert Stork, K Z. *Tetrahedron letters* 1989, 30(17), 2173) (77 mg, 0.144 mmol) in THF (0.6 mL) at room temperature, a 1M solution of sodium hexamethyldisilazane (NaHMDS) in THF (0.144 mL, 0.144 mmol) was slowly added. After stirring for an additional 2 min, the solution was cooled to −78° C. and a solution of aldehyde 25 (18 mg, 0.103 mmol) dissolved in THF (0.5 mL) was added.

The temperature was kept at −78° C. while the reaction mixture was stirred for 2 hours. Hexane (15 mL) was added and the resulting slurry was filtrated over Celite® and washed with additional hexane (30 mL).

The filtrate was evaporated under reduced pressure and the resulting oil was purified by column chromatography (hexane/EtOAc 10:1) affording 22 mg (72% yield) of iodide 26 as a colourless oil.

$^1$H NMR (CDCl$_3$, 300 MHz) δ: 7.34-7.17 (m, 5H), 6.73 (d, 1H, J=8.4 Hz), 6.14 (d, 1H, J=8.4 Hz), 5.83 (d, 1H, J=9.5 Hz), 3.79 (m, 1H), 1.95 (s, 3H), 1.40 (d, 3H, J=7.0 Hz).

$^{13}$C NMR (CDCl$_3$, 75 MHz) δ: 145.9, 142.3, 139.1, 131.9, 128.7, 127.3, 127.2, 126.3, 38.4, 22.1, 16.0

Example 5

Synthesis of Fragment 29

Scheme 5 provides an example of the synthesis of fragment 29.

Scheme 5

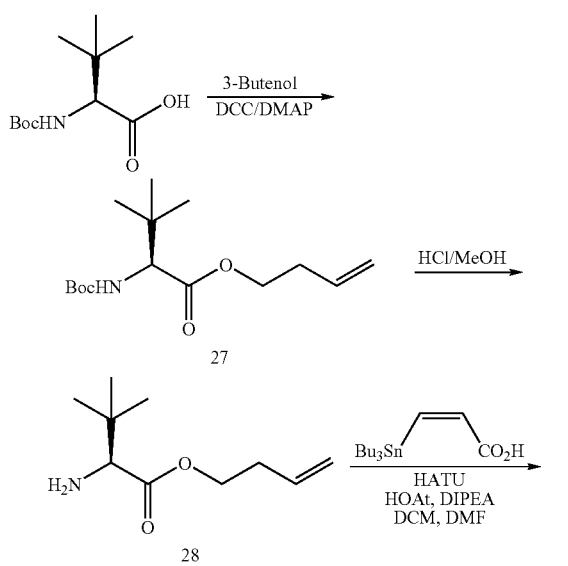

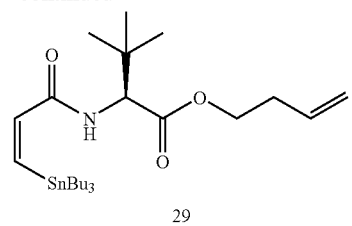
29

Synthesis of Intermediate 27

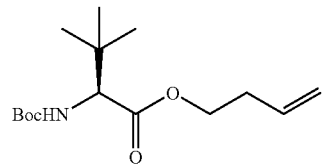 [SMILES: C=CCCOC(=O)[C@@H](NC(=O)OC(C)(C)C)C(C)(C)C]

To a mixture of L-Boc-tert-leucine (300 mg, 1.3 mmol) in DCM anhydrous (13 mL) and Dicyclohexylcarbodiimide (DCC) (295 mg, 1.43 mmol) at 0° C., under N$_2$, the 3-butenol (0.3 mL, 3.9 mmol) and the Dimethylaminopyridine (DMAP) (15.9 mg, 0.13 mmol) were added. The reaction mixture was stirred for 5 minutes at 0° C. and 4 hours at room temperature. The organic solvent was evaporated under reduced pressure and the resulting solid was purified by column chromatography (hexane/EtOAc 10:1) affording 300 mg (yield: 81%) of ester 27.

$^1$H NMR (CDCl$_3$, 300 MHz) δ: 5.82-5.71 (m, 1H), 5.14-5.06 (m, 2H), 4.24-4.12 (m, 2H), 4.08 (d, 1H, J=9.8 Hz), 2.41 (q, 2H, J=6.7 Hz), 1.43 (s, 9H), 0.96 (s, 9H).

Synthesis of Intermediate 28

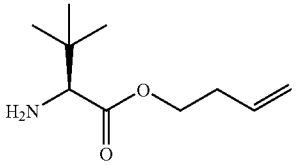

The solution of the ester 27 (180 mg, 0.63 mmol) in HCl.MeOH 1M (3.6 mL) was stirred at room temperature for 24 hours. The organic solvent was evaporated under reduced pressure and the resulting solid was diluted in DCM and washed with H$_2$O. The resulting organic phase was dried over anhydrous Na$_2$SO$_4$, filtered, and the solvent was evaporated to afford 116 mg (yield: 100%) of 28.

$^1$H NMR (CDCl$_3$, 300 MHz) δ: 5.85-5.72 (m, 1H), 5.15-5.06 (m, 2H), 4.16 (t, 2H, J=6.7 Hz), 3.15 (s, 1H), 4.44-4.37 (m, 2H), 0.96 (s, 9H).

Synthesis of Intermediate 29

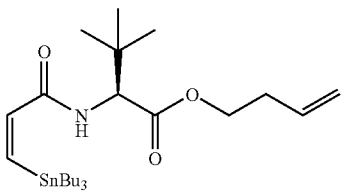

DIPEA (0.24 mL, 1.4 mmol), HOAt (123.3 mg, 0.9 mmol), and HATU (345 mg, 0.9 mmol) were added to a solution of 28 (168 mg, 0.9 mmol), and (Z)-3-tributylstannylpropenoic acid (393 mg, 1.2 mmol) in DCM/DMF (10:1, 14 mL) at 0° C. under $N_2$ atmosphere. After 2 hours, the cold bath was removed and the reaction mixture was stirred at room temperature for 1 h, quenched with a saturated aqueous solution of $NH_4Cl$, poured into water and extracted with DCM. The combined organic phases were dried over anhydrous $Na_2SO_4$, filtered and concentrated. The residue was purified by flash chromatography (Hexane/EtOAc 15:1 to 10:1) to give 29 (340 mg; yield: 72%).

$^1$H NMR (CDCl$_3$, 300 MHz) δ: 7.01 (d, 1H, J=12.3 Hz), 6.75 (d, 1H, J=12.3), 6.03 (d, NH, J=9.73 Hz), 5.84-5.69 (m, 1H), 5.14-5.05 (m, 2H), 4.60 (d, 1H, J=9.76 Hz), 4.19-4.14 (m, 2H), 2.40 (q, 2H, J=6.70 Hz), 1.48-1.40 (m, 6H), 1.31-1.19 (m, 6H), 0.96 (s, 9H), 0.93-0.83 (m, 15H)

Example 6

Scheme 6 provides the synthesis of several compounds of the invention.

Scheme 6

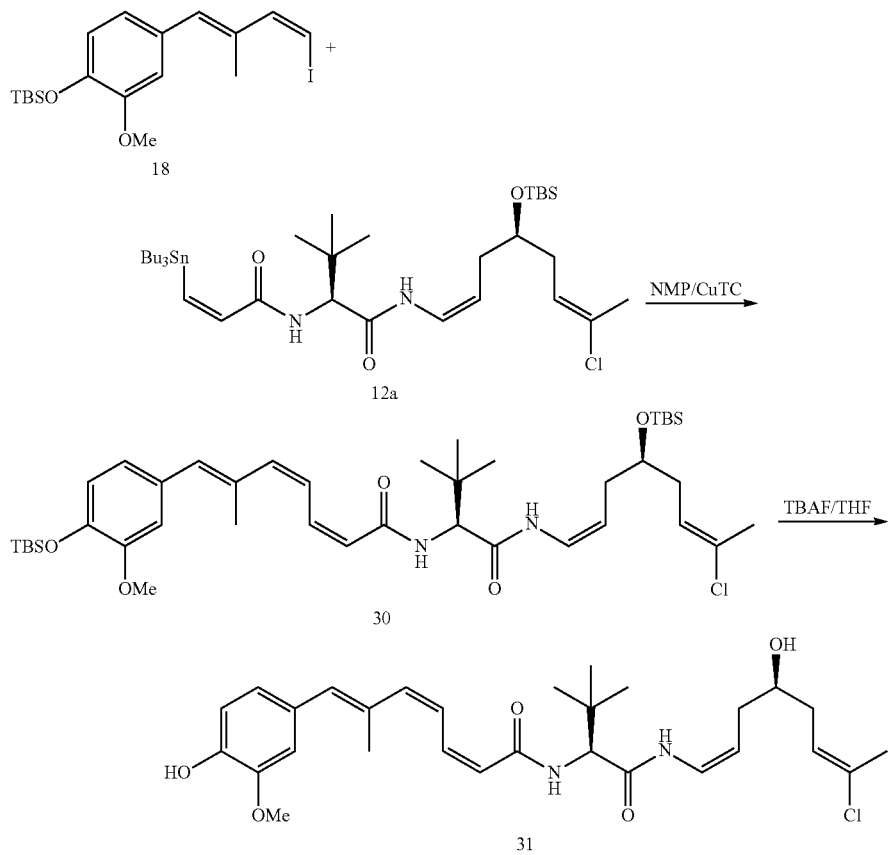

Synthesis of Compound 30

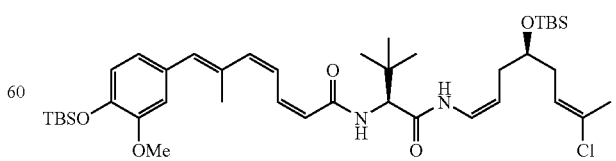

To a solution of alkenylstannane 12a (130 mg, 0.174 mmol) and 18 (90 mg, 0.209 mmol) in 1-methyl-2-pyrrolidinone (NMP) (1.75 mL) at 0° C., Copper thiophenecarboxy late (CuTC) (49.6 mg, 0.261 mmol) was added. The reaction was stirred at 0° C. for 45 min and 20 min at room temperature. Then, the crude mixture was filtered through a plug of neutral alumina, washed with EtOAc/Ether 50:50 and the combined filtrates were washed with HCl 0.5N (3×15 mL). The organic solution was dried and evaporated to give the crude product which was purified by column chromatography (Hexane/EtOAc 8:1 to 1:1) to give triene 30 (65 mg, yield: 49%) as an oil.

$^1$H NMR (CDCl$_3$, 300 MHz) δ: 7.64 (d, 1H, J=11.1 Hz), 7.33 (dd, 1H, J=11.7, 11.4 Hz), 7.04 (dd, 1H, J=12.0, 11.1 Hz), 6.83-6.81 (m, 3H), 6.77-6.70 (m, 1H), 6.45 (br s, 1H), 6.33 (d, 1H, J=11.7 Hz), 6.22 (d, 1H, J=9.0 Hz), 5.64 (d, 1H, J=11.4 Hz), 5.62-5.56 (m, 1H), 4.89-4.80 (m, 1H), 4.36 (d, 1H, J=9.3 Hz), 3.81 (s, 3H), 3.80-3.78 (m, 1H), 2.23-2.14 (m, 4H), 2.08 (s, 3H); 2.03 (s, 3H), 1.05 (s, 9H), 1.00 (s, 9H), 0.89 (s, 9H), 0.17 (s, 6H), 0.08 (s, 3H), 0.06 (s, 3H).

To a solution of 30 (60 mg, 0.08 mmol) in THF (1.5 mL) under N$_2$ and at room temperature, Tetrabutylammonium fluoride (TBAF) 1M in THF (0.23 mL, 0.23 mmol) was added. The reaction was stirred at room temperature for 18 hours and then quenched with a saturated aqueous solution of NH$_4$Cl and extracted with EtOAc. The combined organic phases were dried over anhydrous Na$_2$SO$_4$, filtered, and concentrated. The residue was purified by flash chromatography (Hexane/EtOAc 5:1 to 1:1) to give alcohol 31 (25.4 mg; yield: 60%) as a white solid.

$^1$H NMR (CDCl$_3$, 300 MHz) δ: 8.74 (d, 1H, J=10.2 Hz), 7.77-7.68 (m, 1H), 6.90-6.50 (m, 4H), 6.61-6.57 (m, 3H), 6.36 (d, 1H, J=9.0 Hz), 5.62 (m, 2H), 4.86 (q, 1H, J=8.5 Hz), 4.37 (d, 1H, J=9.0 Hz), 3.90 (s, 3H), 3.77 (m, 1H), 2.67 (bs, 1H), 2.20 (m, 4H), 2.09 (s, 3H), 2.07 (s, 3H), 1.05 (s, 9H).

Synthesis of Compound 31

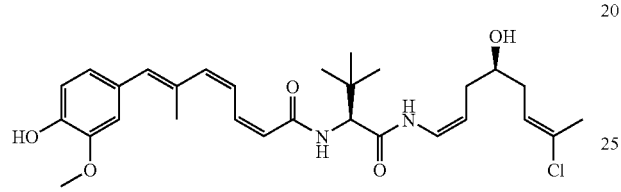

Example 7

Scheme 7 provides the synthesis of several compounds of the invention.

Scheme 7

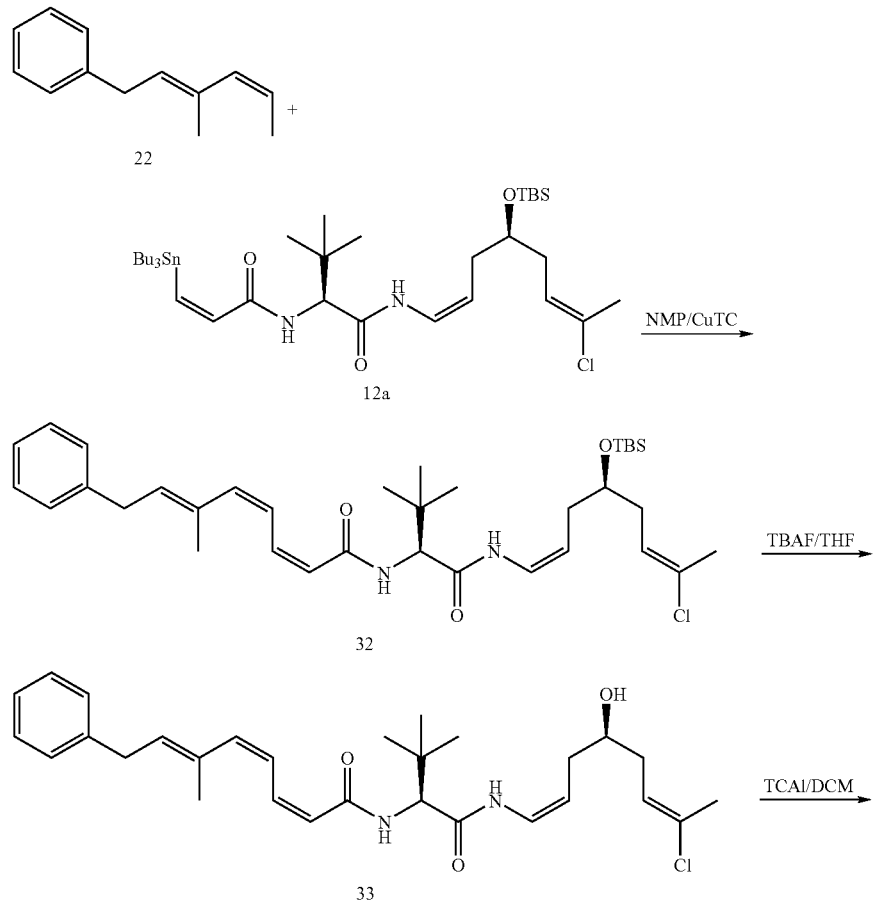

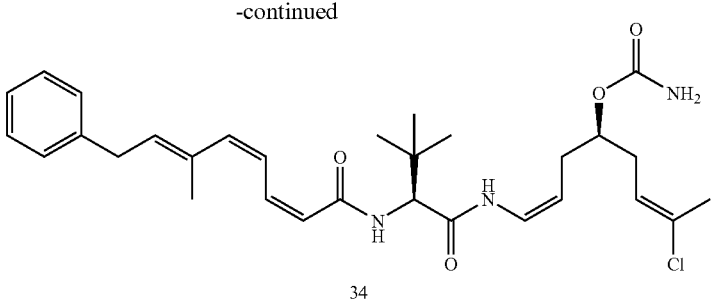

34

Synthesis of Compound 32

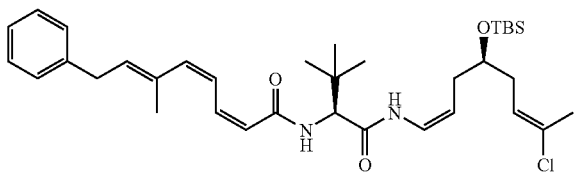

To a solution of alkenylstannane 12a (42 mg, 0.056 mmol) and iodide 22 (20 mg, 0.067 mmol) in 1-methyl-2-pyrrolidinone (NMP) (0.6 mL) at 0° C., Copper thiophenecarboxylate (CuTC) (16 mg, 0.084 mmol) was added. The reaction was stirred at 0° C. for 45 min and 20 min at room temperature. Then, the crude mixture was filtered through a plug of neutral alumina, washed with EtOAc/Ether 50:50 and the combined filtrates were washed with HCl 0.5N (3×5 mL). The organic solution was dried and evaporated to give the crude product which was purified by column chromatography (Hexane/EtOAc 12:1 to 6:1) to give triene 32 (15 mg, yield: 45%) as an oil.

$^1$H NMR (CDCl$_3$, 300 MHz) δ: 7.67 (d, 1H, J=10.8 Hz), 7.35-7.18 (m, 6H), 6.92 (t, 1H, J=11.4 Hz), 6.72 (t, 1H, J=10.8 Hz), 6.22 (m, 2H), 5.69 (t, 1H, J=7.5 Hz), 5.58 (m, 2H), 4.82 (q, 1H, J=8.7 Hz), 4.35 (d, 1H, J=9.3 Hz), 3.75 (m, 1H), 3.49 (d, 2H, J=7.5 Hz), 2.15 (m, 4H), 2.02 (s, 3H), 1.91 (s, 3H), 1.02 (s, 9H), 0.88 (s, 9H), 0.06 (s, 3H), 0.05 (s, 3H).

Synthesis of Compound 33

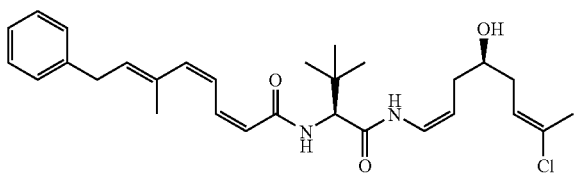 [SMILES: C/C(Cl)=C\C[C@H](O)C/C=C\NC(=O)[C@@H](NC(=O)\C=C/C=C\C(C)=C\Cc1ccccc1)C(C)(C)C]

To a solution of 32 (15 mg, 0.024 mmol) in THF (0.5 mL) under N$_2$ and at room temperature, TBAF 1M in anhydrous THF (0.05 mL, 0.05 mmol) was added. The reaction was stirred at room temperature for 18 hours and then quenched with a saturated aqueous solution of NH$_4$Cl and extracted with EtOAc. The combined organic phases were dried over anhydrous Na$_2$SO$_4$, filtered, and concentrated. The residue was purified by flash chromatography (Hexane/EtOAc 3:1 to 1:2) to give alcohol 33 (4 mg, yield: 35%).

$^1$H NMR (CDCl$_3$, 300 MHz) δ: 8.76 (d, 1H, J=9.6 Hz), 7.35-7.17 (m, 6H), 6.96 (t, 1H, J=11.4 Hz), 6.76 (t, 1H, J=8.4 Hz), 6.21 (m, 2H), 5.69 (t, 1H, J=7.5 Hz), 5.61 (m, 2H), 4.87 (q, 1H, J=8.1 Hz), 4.29 (d, 1H, J=9.3 Hz), 3.77 (m, 1H), 3.49 (d, 2H, J=7.2 Hz), 2.2 (m, 4H), 2.06 (s, 3H), 1.91 (s, 3H), 1.02 (s, 9H).

MS (ES) m/z 499 (M+1)$^+$, 521 (M+Na)$^+$.

Synthesis of Compound 34

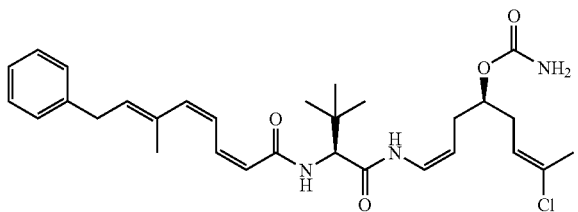 [SMILES: C/C(Cl)=C\C[C@@H](C/C=C\NC(=O)[C@@H](NC(=O)\C=C/C=C\C(C)=C\Cc1ccccc1)C(C)(C)C)OC(N)=O]

To a solution of 33 (3 mg, 0.006 mmol) in Dichloromethane (0.4 mL) at room temperature, trichloroacetyl isocyanate (TCAI) (1 µL, 0.0072 mmol) was added. The reaction was stirred at room temperature for 30 min and then neutral aluminium oxide was added. The mixture was stirred for 30 min and then was soaked into a pad of aluminium oxide. The product was washed out using a mixture of DCM/MeOH 50:1. The filtrate was evaporated in vacuo to give the crude product which was purified by column chromatography (Hexane/EtOAc 3:1 to 2:1) to give compound 34 (2 mg, yield: 63%).

$^1$H NMR (CDCl$_3$, 300 MHz) δ: 8.55 (d, 1H, J=11.4 Hz), 7.35-7.17 (m, 6H), 6.96 (t, 1H, J=11.1 Hz), 6.82 (t, 1H, J=8.4 Hz), 6.32 (d, 1H, J=9.3 Hz), 6.22 (d, 1H, J=10.5 Hz), 5.68 (t, 1H, J=7.5 Hz), 5.62 (m, 2H), 4.81 (q, 1H, J=8.1 Hz), 4.46 (m, 1H), 4.42 (d, 1H, J=9.3 Hz), 3.50 (d, 2H, J=7.2 Hz), 2.34 (m, 4H), 2.06 (s, 3H), 1.91 (s, 3H), 1.03 (s, 9H).

Example 8

Scheme 8 provides the synthesis of several compounds of the invention.

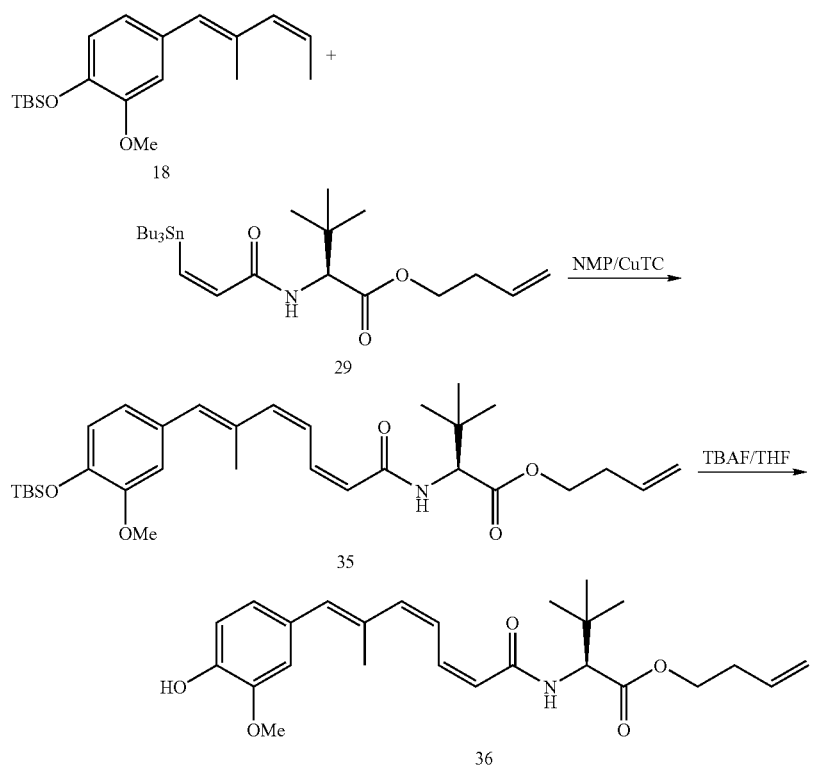

Synthesis of Compound 35

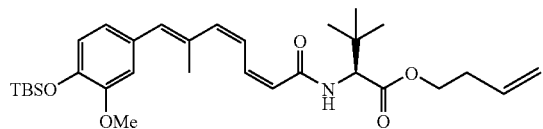 [SMILES: C=CCCOC(=O)[C@@H](NC(=O)\C=C/C=C\C(C)=C\c1ccc(O[Si](C)(C)C(C)(C)C)c(OC)c1)C(C)(C)C]

Synthesis of Compound 36

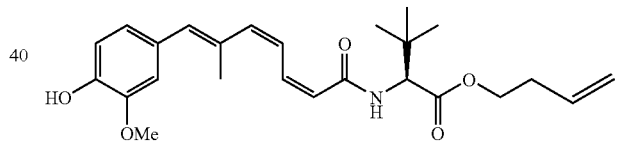

To a solution of 29 (25 mg, 0.05 mmol) and 18 (31 mg, 0.06 mmol) in NMP (0.5 mL) at 0° C., Copper thiophenecarboxylate (CuTc, 13.5 mg, 1.5 mmol) was added. The reaction was stirred at 0° C. for 45 min and at room temperature for an hour. Then, the crude mixture was filtered through a plug of neutral alumina, washed with EtOAc/Ether 50:50 (20 mL) and the combined filtrates were washed with HCl 0.5N (3×10 mL). After drying and evaporating the solvent under reduced pressure the crude was purified by column chromatography (EtOAc/hexane, from 10:1 to 5:1) to afford pure 35 (5 mg, yield: 18%).

$^1$H NMR (CDCl$_3$, 300 MHz) δ: 7.38 (m, 1H), 7.04 (m, 1H), 6.83-6.81 (m, 3H), 6.46 (s, 1H), 6.32 (d, 1H, J=11.1 Hz), 6.03 (d, 1H, J=9.3 Hz), 5.77 (m, 1H), 5.64 (d, 1H, J=11.4 Hz), 5.16-5.07 (m, 2H), 4.55 (d, 1H, J=9.6 Hz), 4.18 (m, 2H), 3.81 (s, 3H), 2.42 (m, 2H), 2.08 (s, 3H), 1.00 (m, 18H), 0.16 (s, 3H), 0.06 (s, 3H).

A solution of 35 (4 mg, 0.007 mmol) in HCl.MeOH 1M (1.2 mL) was stirred at room temperature for 2 hours and 30 min. The organic solvent was evaporated under reduced pressure and the resulting crude was purified by column chromatography (Ethyl acetate/hexane 10:1-1:10) to afford pure 36 (1.8 mg, yield: 60%).

$^1$H NMR (CDCl$_3$, 300 MHz) δ: 7.31-7.26 (m, 1H), 7.00-6.92 (m, 4H), 6.60-6.55 (m, 2H), 6.03 (d, 1H, J=9.0 Hz), 5.82-5.71 (m, 1H), 5.65 (d, 1H, J=10.5 Hz), 5.14-5.06 (m, 2H), 4.58 (d, 1H, J=9.5 Hz), 4.17-4.08 (m, 2H), 3.90 (s, 3H), 2.54-2.39 (m, 2H), 2.01 (s, 3H), 1.03 (s, 9H).

Example 9

Scheme 9 provides the synthesis of several compounds of the invention.

Scheme 9

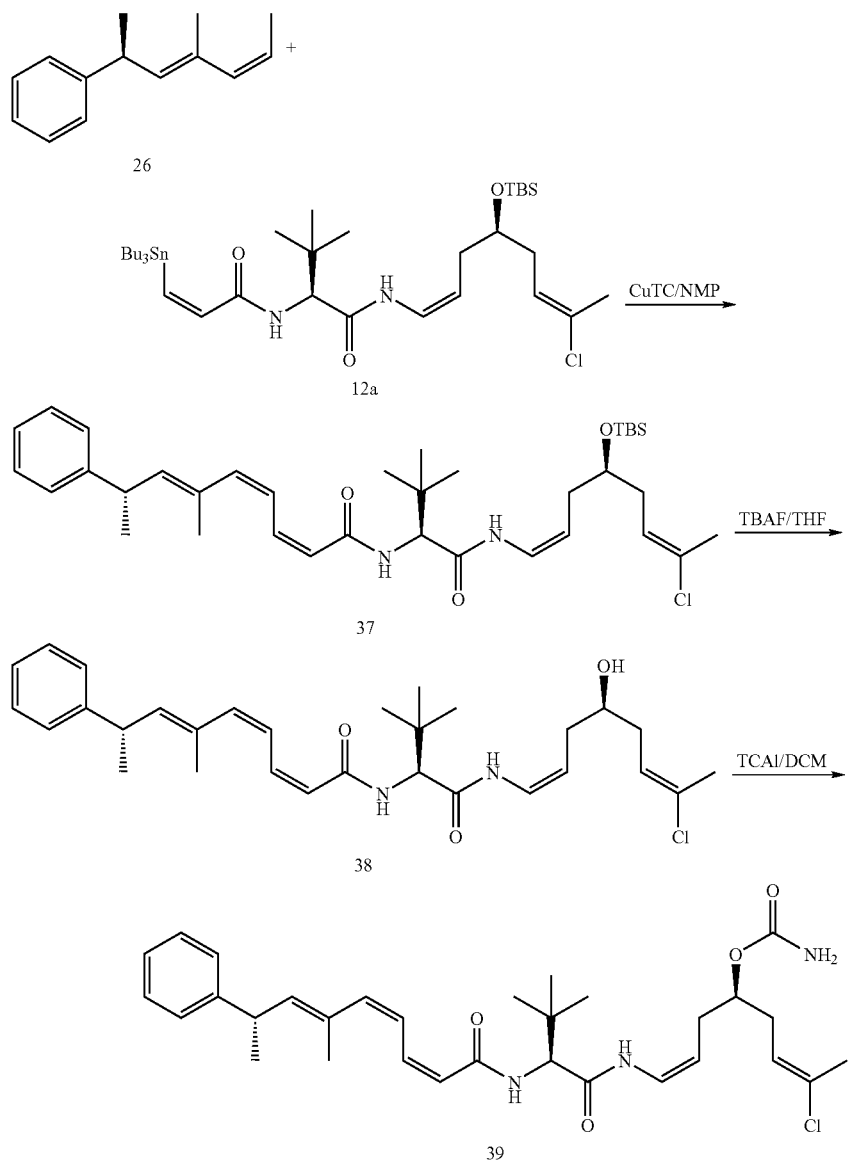

Synthesis of Compound 37

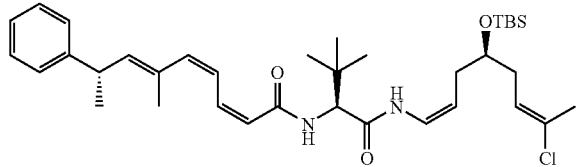 [SMILES: C/C(Cl)=C\C[C@@H](C/C=C\NC(=O)[C@@H](NC(=O)\C=C/C=C\C(C)=C\[C@H](C)c1ccccc1)C(C)(C)C)O[Si](C)(C)C(C)(C)C]

To a solution of 12a (42 mg, 0.056 mmol) and iodide 26 (20 mg, 0.067 mmol) in 1-methyl-2-pyrrolidinone (NMP) (0.6 mL) at 0° C., Copper thiophenecarboxylate (CuTC) (16 mg, 0.084 mmol) was added. The reaction was stirred at 0° C. for 45 min and at room temperature for 20 minutes. Then, the crude mixture was filtered through a plug of neutral alumina, washed with EtOAc/Et$_2$O 50:50 and the combined filtrates were washed with HCl 0.5N (3×5 mL). The organic solution was dried and evaporated to give the crude product which was purified by column chromatography (hexane/EtOAc 7:1 to 5:1) to give triene 37 (9 mg, 26% yield) as an oil.

$^1$H NMR (CDCl$_3$, 300 MHz) δ: 7.63 (d, 1H, J=10.5 Hz), 7.33-7.15 (m, 6H), 6.90 (t, 1H, J=11.6 Hz), 6.73 (t, 1H, J=10.1 Hz), 6.19 (m, 2H), 5.61 (m, 3H), 4.82 (q, 1H, J=8.8 Hz), 4.34 (d, 1H, J=9.3 Hz), 3.76 (m, 2H), 2.16 (m, 4H), 2.02 (s, 3H), 1.85 (s, 3H), 1.37 (d, 3H, J=7.0 Hz), 1.03 (s, 9H), 0.88 (s, 9H), 0.07 (s, 3H), 0.05 (s, 3H).

$^{13}$C NMR (CDCl$_3$, 75 MHz) δ: 168.4, 166.4, 146.2, 141.2, 139.9, 137.9, 131.6, 131.2, 128.7, 127.1, 126.3, 124.0, 123.7, 122.5, 120.3, 108.6, 71.6, 60.6, 38.8, 36.5, 35.1, 33.8, 29.9, 26.8, 26.1, 22.4, 21.3, 17.1, −4.3, −4.4.

Synthesis of Compound 38

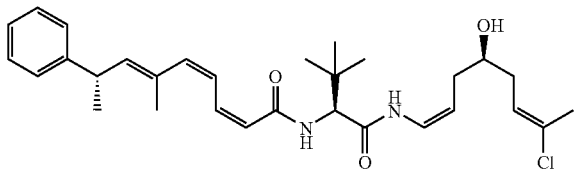 [SMILES: C/C(Cl)=C\C[C@H](O)C/C=C\NC(=O)[C@@H](NC(=O)\C=C/C=C\C(C)=C\[C@H](C)c1ccccc1)C(C)(C)C]

To a solution of 37 (9 mg, 0.014 mmol) in THF (0.3 mL) under $N_2$ and at room temperature, TBAF 1M in THF (0.028 mL, 0.028 mmol) was added. The reaction was stirred at room temperature for 7 hours and then quenched with a saturated aqueous solution of $NH_4Cl$ and extracted with EtOAc. The combined organic phases were dried over anhydrous $Na_2SO_4$, filtered, and concentrated. The residue was purified by flash chromatography (hexane/EtOAc 3:1 to 1:1) to give alcohol 38 (4.5 mg, 62.5% yield) as a colourless oil.

$^1$H NMR (CDCl$_3$, 300 MHz) δ: 8.80 (d, 1H, J=10.2 Hz), 7.34-7.19 (m, 6H), 6.91 (t, 1H, J=11.7 Hz), 6.76 (t, 1H, J=9.2 Hz), 6.34 (d, 1H, J=8.8 Hz), 6.19 (d, 1H, J=11.6 Hz), 5.62 (m, 3H), 4.85 (q, 1H, J=8.2 Hz), 4.33 (d, 1H, J=9.2 Hz), 3.75 (m, 2H), 2.77 (bs, 1H) 2.18 (m, 4H), 2.06 (s, 3H), 1.85 (s, 3H), 1.36 (d, 3H, J=7.0 Hz), 1.03 (s, 9H).

Synthesis of Compound 39

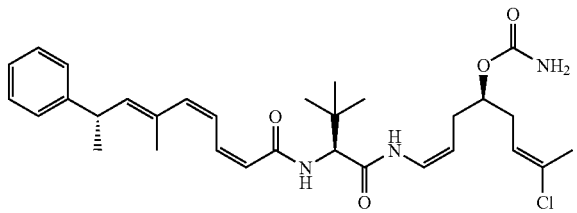 [SMILES: C/C(Cl)=C\C[C@@H](C/C=C\NC(=O)[C@@H](NC(=O)\C=C/C=C\C(C)=C\[C@H](C)c1ccccc1)C(C)(C)C)OC(N)=O]

To a solution of 38 (3 mg, 0.006 mmol) in dichloromethane (0.5 mL) at room temperature, trichloroacetyl isocyanate (TCAI) (1 µL, 0.0069 mmol) was added. The reaction was stirred at room temperature for 30 min and then neutral aluminium oxide (44 mg) was added. The mixture was stirred for 30 min and then was soaked into a pad of aluminium oxide. The product was washed out using a mixture of dichloromethane/MeOH 50:1. The filtrate was evaporated under reduced pressure to give the crude product which was purified by column chromatography (hexane/EtOAc 3:1 to 1:1) to give compound 39 (1.6 mg, 50% yield) as a colourless oil.

$^1$H NMR (CDCl$_3$, 300 MHz) δ: 8.58 (d, 1H, J=10.8 Hz), 7.32-7.19 (m, 6H), 6.91 (t, 1H, J=11.6 Hz), 6.84 (t, 1H, J=9.0 Hz), 6.33 (d, 1H, J=9.8 Hz), 6.18 (d, 1H, J=10.7 Hz), 5.61 (m, 3H), 4.80 (q, 1H, J=8.9 Hz), 4.45 (m, 1H), 4.40 (d, 1H, J=9.5 Hz), 3.77 (m, 1H), 2.34 (m, 4H), 2.07 (s, 3H), 1.86 (s, 3H), 1.36 (d, 3H, J=7.0 Hz), 1.04 (s, 9H).

MS (ES) m/z 578.2 [M+Na]$^+$.

Example 10

Bioassays for the Detection of Antitumor Activity

The aim of this assay is to evaluate the in vitro cytostatic (ability to delay or arrest tumor cell growth) or cytotoxic (ability to kill tumor cells) activity of the samples being tested.

Cell Lines

| Name | N° ATCC | Species | Tissue | Characteristics |
|---|---|---|---|---|
| A549 | CCL-185 | human | lung | lung carcinoma (NSCLC) |
| HT29 | HTB-38 | human | colon | colorectal adenocarcinoma |
| MDA-MB-231 | HTB-26 | human | breast | breast adenocarcinoma |

Evaluation of Cytotoxic Activity Using the SBR Colorimetric Assay

A colorimetric type of assay, using sulforhodamine B (SRB) reaction has been adapted for a quantitative measurement of cell growth and viability (following the technique described by Skehan P et al. J. Natl. Cancer Inst. 1990, 82, 1107-1112).

This form of assay employs SBS-standard 96-well cell culture microplates (Faircloth et al. Methods in Cell Science, 1988, 11(4), 201-205; Mosmann et al, Journal of Immunological. Methods, 1983, 65(1-2), 55-63). All the cell lines used in this study, derived from different types of human cancer, were obtained from the American Type Culture Collection (ATCC).

Cells were maintained in Dulbecco's Modified Eagle Medium (DMEM) supplemented with 10% Fetal Bovine Serum (FBS), 2 mM L-glutamine, 100 U/mL penicillin and 100 U/mL streptomycin at 37° C., 5% $CO_2$ and 98% humidity. For the experiments, cells were harvested from subconfluent cultures using trypsinization and resuspended in fresh medium before counting and plating.

Cells were seeded in 96 well microtiter plates at 5×10$^3$ cells per well in aliquots of 150 µL, and allowed to attach to the plate surface for 18 hours in drug free medium. One control (untreated) plate of each cell line was fixed (as described below) and used for time zero reference value. Afterwards, test samples were added to the cultures in ten serial dilutions, in aliquots of 50 µL, ranging from 10 to 0.00262 µg/mL. After 48 hours exposure, the antitumor effect was estimated by the SRB method: Briefly, cells were washed twice with PBS, fixed for 15 min in 1% glutaraldehyde solution, rinsed twice in PBS, and stained in 0.4% SRB solution for 30 min at room temperature. Cells were then rinsed several times with 1% acetic acid solution and air-dried. SRB was then extracted in 10 mM trizma base solution and the absorbance measured in an automated spectrophotometric plate reader at 490 nm. Cell survival was expressed as percentage of control cell growth. The final effect of the sample being tested was estimated by applying the NCI algorithm (Boyd M R and Paull K D. Drug Dev. Res. 1995, 34, 91-104).

Using the mean±SD of triplicate cultures, a dose-response curve was automatically generated using nonlinear regression analysis. Three reference parameters were calculated (NCI algorithm) by automatic interpolation: GI$_{50}$=concentration that produces 50% growth inhibition; TGI=total growth inhibition (cytostatic effect) and LC$_{50}$=concentration that produces 50% net cell killing (cytotoxic effect).

Table 1 illustrates data on the biological activity of compounds of the present invention.

TABLE 1

| Cytotoxicity assay - Activity Data (Molar) | | | | | |
| --- | --- | --- | --- | --- | --- |
| | | Compound 30 | Compound 32 | Compound 33 | Compound 34 |
| MDA-MB-231 | $GI_{50}$ | 7.64E−07 | 8.33E−07 | 3.01E−06 | 1.03E−06 |
| | TGI | 9.74E−07 | 1.11E−06 | 4.81E−06 | 4.43E−06 |
| | $LC_{50}$ | 1.26E−06 | 1.50E−06 | 8.01E−06 | >1.84E−05 |
| A549 | $GI_{50}$ | 6.71E−07 | 4.90E−07 | 1.58E−06 | 7.01E−07 |
| | TGI | 7.64E−07 | 6.86E−07 | 3.41E−06 | 2.77E−06 |
| | $LC_{50}$ | 9.08E−07 | 1.06E−06 | 7.41E−06 | >1.84E−05 |
| HT29 | $GI_{50}$ | 7.77E−07 | 4.90E−07 | 1.10E−06 | 4.43E−07 |
| | TGI | 8.16E−07 | 6.21E−07 | 1.82E−06 | 5.72E−07 |
| | $LC_{50}$ | 8.69E−07 | 8.49E−07 | 3.81E−06 | 9.04E−07 |
| | | Compound 36 | Compound 37 | Compound 38 | Compound 39 |
| MDA-MB-231 | $GI_{50}$ | 1.15E−06 | 5.26E−6 | 2.14E−6 | 9.17E−8 |
| | TGI | 2.57E−06 | 7.01E−6 | 4.48E−6 | 2.70E−7 |
| | $LC_{50}$ | 1.92E−05 | 9.40E−6 | >1.95E−5 | >1.80E−5 |
| A549 | $GI_{50}$ | 3.27E−06 | 2.87E−6 | 1.81E−6 | 5.57E−8 |
| | TGI | >2.34E−05 | 5.90E−6 | 4.87E−6 | >1.80E−5 |
| | $LC_{50}$ | >2.34E−05 | 1.08E−5 | >1.95E−5 | >1.80E−5 |
| HT29 | $GI_{50}$ | 1.96E−06 | 3.67E−6 | 1.09E−6 | 3.60E−8 |
| | TGI | 7.95E−06 | 4.46E−6 | 1.52E−6 | 5.93E−8 |
| | $LC_{50}$ | >2.34E−05 | 5.90E−6 | 4.68E−6 | 3.60E−7 |

The invention claimed is:

1. A compound of general formula I

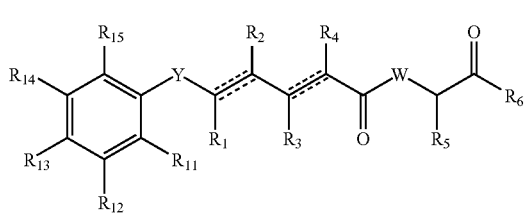

(I)

wherein Y is selected from —$CHR_{ay}$—, —$CHR_{ay}$—$CHR_{by}$—, —$CR_{ay}$=$CR_{by}$—, —C≡C—, —$CHR_{ay}$—$CHR_{by}$—$CHR_{cy}$—, —$CHR_{ay}$—$CR_{by}$=$CR_{cy}$—, and —$CHR_{ay}$—C≡C—;

each $R_{ay}$, $R_{by}$, and $R_{cy}$ is independently selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

each $R_1$, $R_2$, $R_3$, $R_4$, and $R_5$ is independently selected from hydrogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl;

$R_6$ is selected from $NR_8R_9$, and $OR_{10}$;

W is selected from O and $NR_7$;

$R_7$ is selected from hydrogen, $COR_a$, $COOR_a$, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl, or $R_7$ and $R_5$ together with the corresponding N atom and C atom to which they are attached may form a substituted or unsubstituted heterocyclic group;

$R_8$ is selected from hydrogen, $COR_a$, $COOR_a$, substituted or unsubstituted $C_2$-$C_{12}$ alkenyl, substituted or unsubstituted $C_2$-$C_{12}$ alkynyl, and substituted or unsubstituted $C_4$-$C_{12}$ alkenynyl;

$R_{10}$ is selected from substituted or unsubstituted $C_2$-$C_{12}$ alkenyl, and substituted or unsubstituted $C_2$-$C_{12}$ alkynyl;

each dotted line represents an optional additional bond with the proviso that one or more additional bonds are present, but when a triple bond exists between the C atoms to which $R_1$ and $R_2$ are attached, $R_1$ and $R_2$ are absent, and when a triple bond exists between the C atoms to which $R_3$ and $R_4$ are attached, $R_3$ and $R_4$ are absent;

$R_9$ is selected from hydrogen, $COR_a$, $COOR_a$, substituted or unsubstituted $C_2$-$C_{12}$ alkenyl, substituted or unsubstituted $C_2$-$C_{12}$ alkynyl, and substituted or unsubstituted $C_4$-$C_{12}$ alkenynyl;

each $R_{11}$, $R_{12}$, $R_{13}$, $R_{14}$, and $R_{15}$ are independently selected from hydrogen, halogen, $OR_a$, $COR_a$, $COOR_a$, $OCOR_a$, $OCOOR_a$, $OCONR_aR_b$, $CONR_aR_b$, $OS(O)R_a$, $OSO_2R_a$, $OP(O)(R_a)OR_b$, $OSiR_aR_bR_c$, $NR_aR_b$, $NR_aCOR_b$, $NR_aCONR_aR_b$, $NR_aS(O)R_b$, $NR_aSO_2R_b$, $NR_aC(=NR_a)NR_aR_b$, $SR_a$, $S(O)R_a$, $SO_2R_a$, $S(O)NR_aR_b$, $SO_2NR_aR_b$, $S(O)OR_a$, $SO_2OR_a$, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl; and each $R_a$, $R_b$, and $R_c$ are independently selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl and substituted or unsubstituted heterocyclic group; or a pharmaceutically acceptable salt, tautomer, or stereoisomer thereof.

2. A compound according to claim 1 wherein $R_1$, $R_2$, $R_3$ and $R_4$ are independently selected from hydrogen and a substituted or unsubstituted $C_1$-$C_6$ alkyl.

3. A compound according to claim 2 wherein $R_1$, $R_2$, $R_3$ and $R_4$ are hydrogen.

4. A compound according to claim 1, wherein $R_{11}$, $R_{14}$ and $R_{15}$ are hydrogen.

5. A compound according to claim 1, wherein Y is selected from —$CHR_{ay}$—, —$CR_{ay}$=$CR_{by}$— and —$CHR_{ay}$—$CR_{by}$=$CR_{cy}$—, and wherein $R_{ay}$, $R_{by}$ and $R_{cy}$ are independently selected from hydrogen and substituted or unsubstituted $C_1$-$C_6$ alkyl.

6. A compound according to claim 5, wherein $R_{ay}$, $R_{by}$ and $R_{cy}$ are independently selected from hydrogen and methyl.

7. A compound according to claim 1, wherein $R_{12}$ and $R_{13}$ are independently selected from hydrogen, $OR_a$, $OCOR_a$ and $OSiR_aR_bR_c$, and wherein $R_a$, $R_b$ and $R_c$ are independently selected from hydrogen and a substituted or unsubstituted $C_1$-$C_6$ alkyl.

8. A compound according to claim 7, wherein $R_{12}$ is selected from hydrogen and $OR_a$.

9. A compound according to claim 7, wherein $R_{13}$ is selected from hydrogen, $OR_a$ and $OSiR_aR_bR_c$.

10. A compound according to claim 7, wherein $R_a$, $R_b$, and $R_c$ are independently selected from hydrogen, substituted or unsubstituted methyl, substituted or unsubstituted ethyl, substituted or unsubstituted propyl, substituted or unsubstituted isopropyl, substituted or unsubstituted tert-butyl.

11. A compound according to claim 1, wherein $R_5$ is selected from hydrogen and a substituted or unsubstituted $C_1$-$C_6$ alkyl.

12. A compound according to claim 11, wherein $R_5$ is selected from methyl, isopropyl and tert-butyl.

13. A compound according to claim 1, wherein W is $NR_7$ and wherein $R_7$ is as defined in claim 1.

14. A compound according to claim 13, wherein $R_7$ is hydrogen.

15. A compound according to claim 1, wherein W is $NR_7$ and wherein $R_7$ and $R_5$ together with the corresponding N atom and C atom to which they are attached form a substituted or unsubstituted pyrrolidine group.

16. A compound according to claim 1, wherein $R_6$ is $NR_9R_9$ and wherein $R_8$ is hydrogen and $R_9$ is selected from hydrogen, substituted or unsubstituted $C_2$-$C_{12}$ alkenyl, substituted or unsubstituted $C_2$-$C_{12}$ alkynyl, and substituted or unsubstituted $C_4$-$C_{12}$ alkenynyl.

17. A compound according to claim 16, wherein $R_9$ is a substituted $C_2$-$C_{12}$ alkenyl that is substituted in one or more positions with halogen, OR', =O, OCOR', OCONHR', OCONR'R', CONHR', CONR'R' and protected OH, wherein each of the R' groups is independently selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl and substituted or unsubstituted aryl.

18. A compound according to claim 1, wherein one additional bond is present between the C atoms to which $R_1$ and $R_2$ are attached and another additional bond is present between the C atoms to which $R_3$ and $R_4$ are attached.

19. A compound according to claim 1, having the following formula:

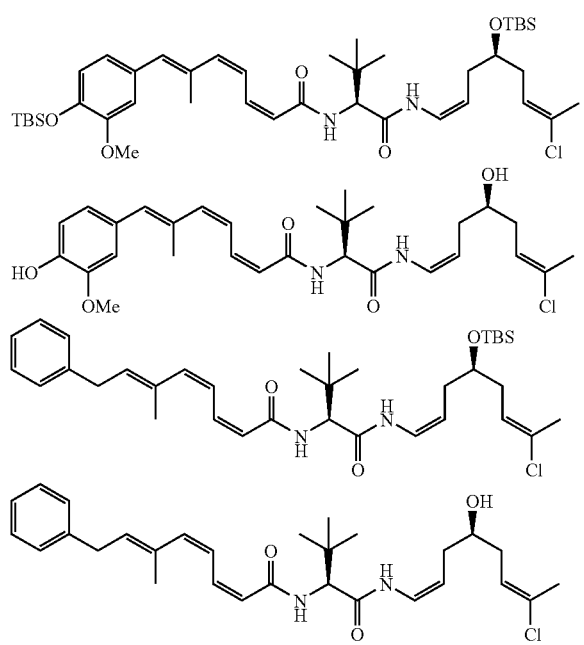

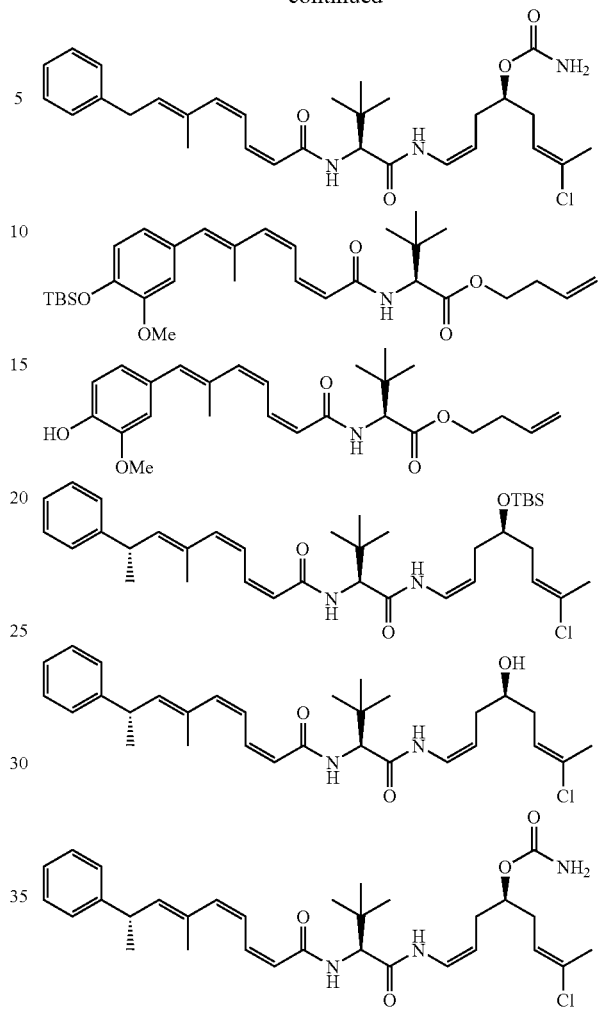

or a pharmaceutically acceptable salt, tautomer, or stereoisomer thereof.

20. A pharmaceutical composition comprising a compound according to any preceding claim, or a pharmaceutically acceptable salt, tautomer, or stereoisomer thereof, and a pharmaceutically acceptable diluent or carrier.

* * * * *

UNITED STATES PATENT AND TRADEMARK OFFICE
CERTIFICATE OF CORRECTION

PATENT NO.        : 8,710,264 B2
APPLICATION NO.   : 12/746966
DATED             : April 29, 2014
INVENTOR(S)       : Alberto Rodriguez Vincente et al.

It is certified that error appears in the above-identified patent and that said Letters Patent is hereby corrected as shown below:

In the Specification

In column 15, lines 27-28, the subscript text is mistyped:

Delete: "Particularly preferred $R_s$ is hydrogen"

and insert -- Particularly preferred $R_5$ is hydrogen --

In columns 19 and 20, lines 50-60, in Scheme 1, the iodine atom is missing:

Delete: " 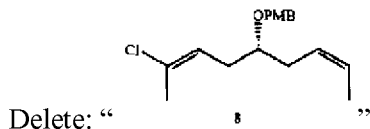 "

and insert -- 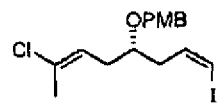 --

In column 31, lines 1-7, in Scheme 2, the iodine atom is missing:

Delete: " 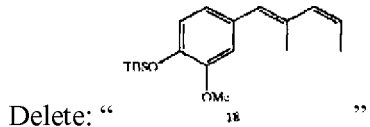 "

Signed and Sealed this
Nineteenth Day of August, 2014

Michelle K. Lee
*Deputy Director of the United States Patent and Trademark Office*

CERTIFICATE OF CORRECTION (continued)
U.S. Pat. No. 8,710,264 B2 and insert -- 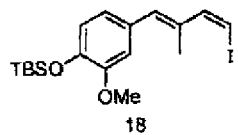 --

In column 33, lines 26-34, in Scheme 3, the iodine atom is missing:

Delete: " 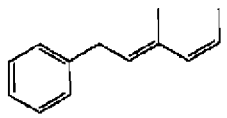 "

and insert -- 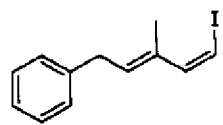 --

In column 34, lines 42-49, in the "Synthesis of Intermediate 22" section, the iodine atom is missing:

Delete: " 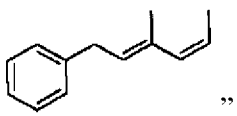 "

and insert -- 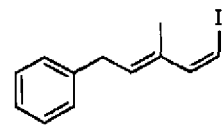 --

In column 35, lines 35-43, in Scheme 4, the iodine atom is missing:

Delete: " 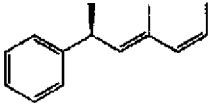 "

and insert -- 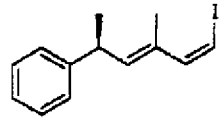 --

In columns 41 and 42, lines 32-40, in Scheme 7, the iodine atom is missing:
Delete: " 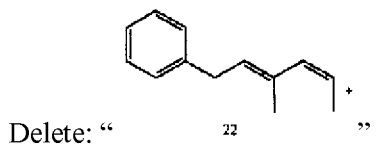 "
and insert -- 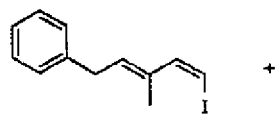 --
In column 45, lines 1-8, in Scheme 8, the iodine atom is missing:
Delete: " 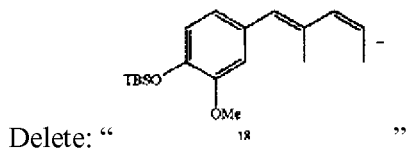 "
and insert -- 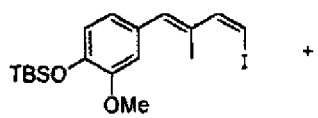 --
In column 47, lines 1-8, in Scheme 9, the iodine atom is missing:
Delete: " 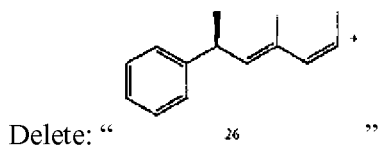 "
and insert -- 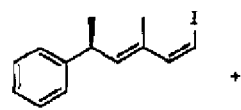 --

UNITED STATES PATENT AND TRADEMARK OFFICE
CERTIFICATE OF CORRECTION

PATENT NO.        : 8,710,264 B2
APPLICATION NO.   : 12/746966
DATED             : April 29, 2014
INVENTOR(S)       : Alberto Rodriguez Vicente et al.

It is certified that error appears in the above-identified patent and that said Letters Patent is hereby corrected as shown below:

In the Specification

In columns 19 and 20, lines 60-70, in Scheme 1, the iodine atom is missing:

Delete: " 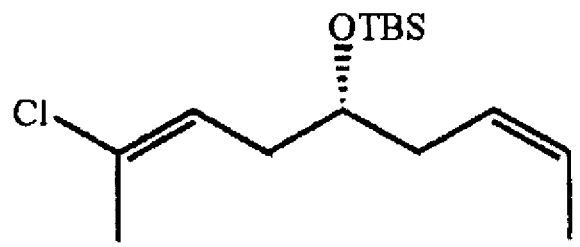 9  "

And insert: -- 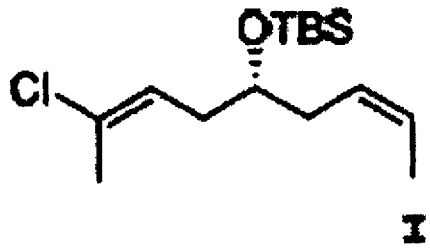 9  --

Signed and Sealed this
Tenth Day of February, 2015

Michelle K. Lee
*Deputy Director of the United States Patent and Trademark Office*